(12) United States Patent
Katzir

(10) Patent No.: US 7,384,581 B2
(45) Date of Patent: Jun. 10, 2008

(54) FORMING TRANSPARENT CRYSTALLINE ELEMENTS BY COLD WORKING

(75) Inventor: Abraham Katzir, Him 15, Afeka, Tel Aviv 69696 (IL)

(73) Assignee: Abraham Katzir, Tel-Aviv (IL)

( * ) Notice: Subject to any disclaimer, the term of this patent is extended or adjusted under 35 U.S.C. 154(b) by 566 days.

(21) Appl. No.: 10/456,631

(22) Filed: Jun. 9, 2003

(65) Prior Publication Data

US 2003/0222380 A1 Dec. 4, 2003

Related U.S. Application Data

(63) Continuation-in-part of application No. 10/138,581, filed on May 6, 2002, now abandoned, which is a continuation of application No. 09/458,688, filed on Dec. 10, 1999, now abandoned.

(60) Provisional application No. 60/111,929, filed on Dec. 11, 1998.

(51) Int. Cl.
*B28B 5/00* (2006.01)
*G02B 1/00* (2006.01)
(52) U.S. Cl. .................................... 264/1.21; 264/1.23
(58) Field of Classification Search ................. 264/1.2, 264/1.23, 1.21
See application file for complete search history.

(56) References Cited

U.S. PATENT DOCUMENTS 4,253,731 A * 3/1981 Anderson et al. ............ 385/142
5,182,790 A * 1/1993 Kayashima et al. ......... 385/141
5,186,870 A * 2/1993 Fuller et al. ................ 264/1.23

FOREIGN PATENT DOCUMENTS

JP 10074983 A * 3/1998

* cited by examiner

*Primary Examiner*—Carlos Lopez
(74) *Attorney, Agent, or Firm*—Mark M. Friedman

(57) ABSTRACT

An infrared optical element, and methods for its manufacture. The optical element is made by cold working an ingot of a soft crystalline ionic solid such as silver halide or a thallium halide inside a sacrificial split die. The solid preferably includes at most one part per million of metallic impurities and at most ten parts per million total impurities. Preferably, the Knoop hardness of the ionic solid is at most about 20, and the elongation ratio of the ionic solid is at least 10% at a temperature of 120-180° C. The optical element maybe a bulk element or a surface element. The optical element may be a refractive element, a diffractive element or a hybrid element. One such element is a flat sensor for attenuated total reflection spectroscopy. In one embodiment of the sensor, a thin layer of silver halide or thallium halide is formed by diffusion or deposition on the surface of a substrate having a lower index of refraction than the layer. The sensor also includes a mechanism for coupling infrared radiation in and out of the layer. The scope of the invention includes a cell for attenuated total reflection spectroscopy based on the sensor, and a spectrometer for attenuated total reflection spectroscopy based on the cell. It also includes an external sensor, which is connected to the spectrometer via two long infrared fibers, which enable measurements in remote locations.

8 Claims, 23 Drawing Sheets

Prior Art

Prior Art

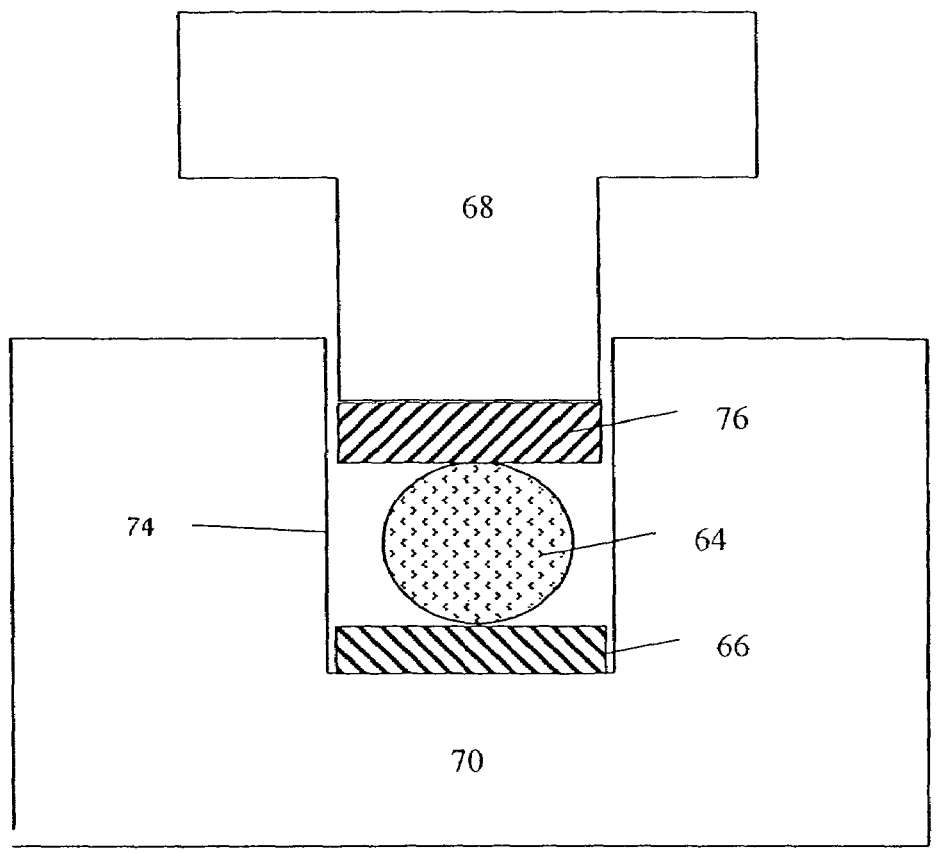
(A)  Press Forging
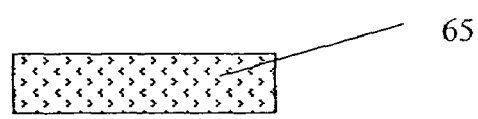
(B) Press Forged Element (e.g. Window)
FIGURE 5 (prior art)

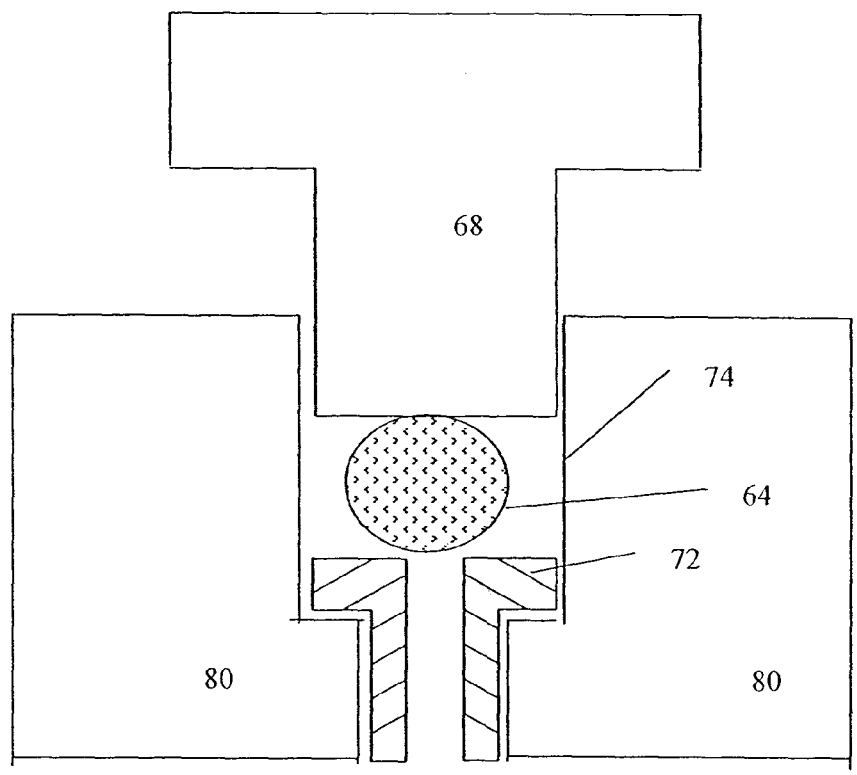
(A) Extrusion System
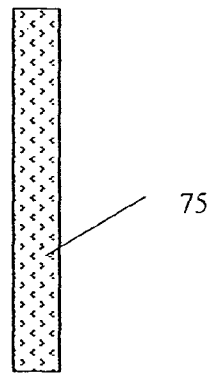
(B) Resulting Optical Element (i.e. optical fiber)
FIGURE 6 (prior art)

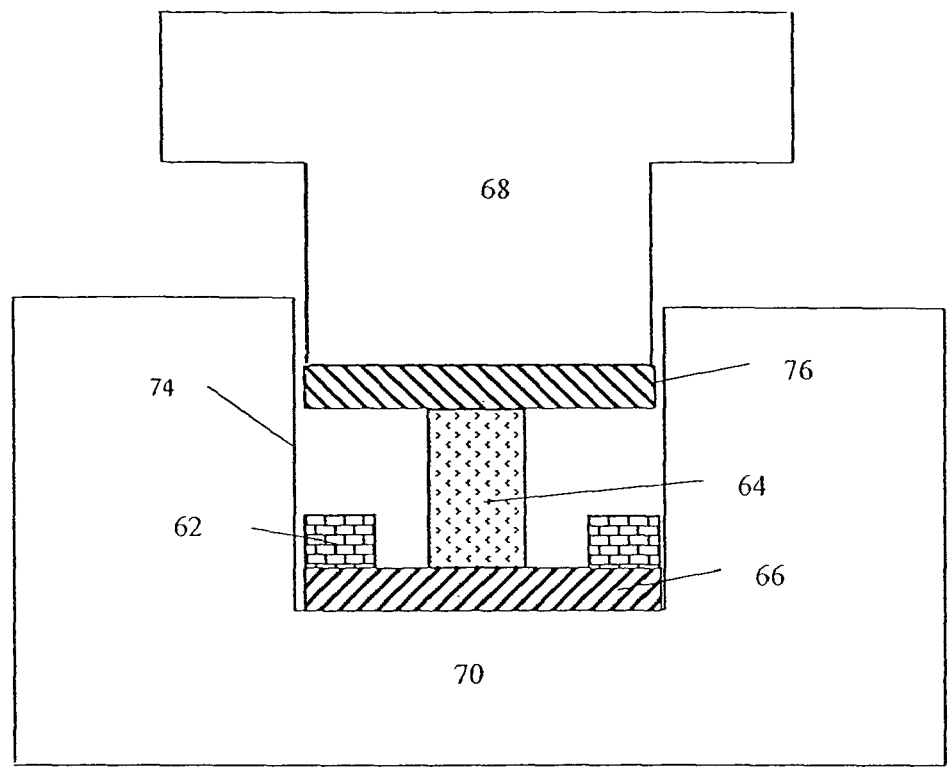
(A) Press forging inside a split die
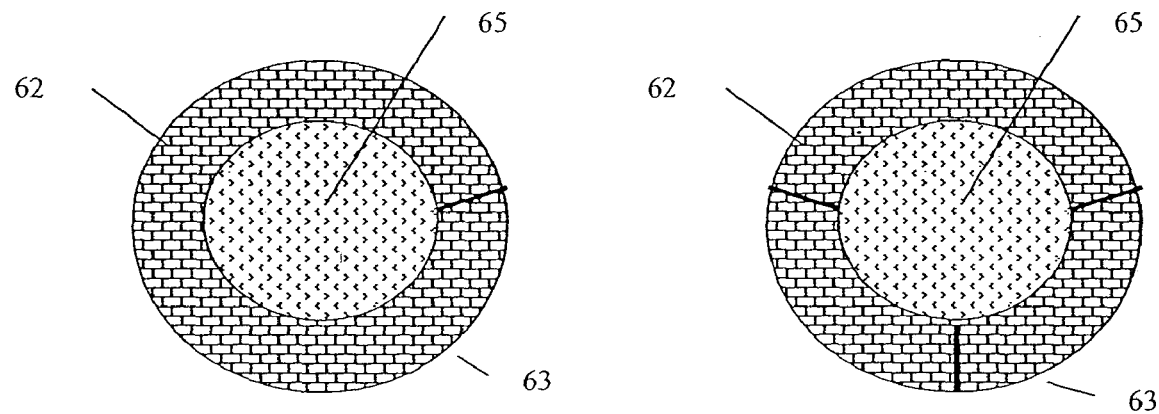
(C) Press Forged Optical element inside a split die that consists of one segment
(B) Press Forged Optical Element (e.g. Window) inside the split die which consists of three segments
FIGURE 7

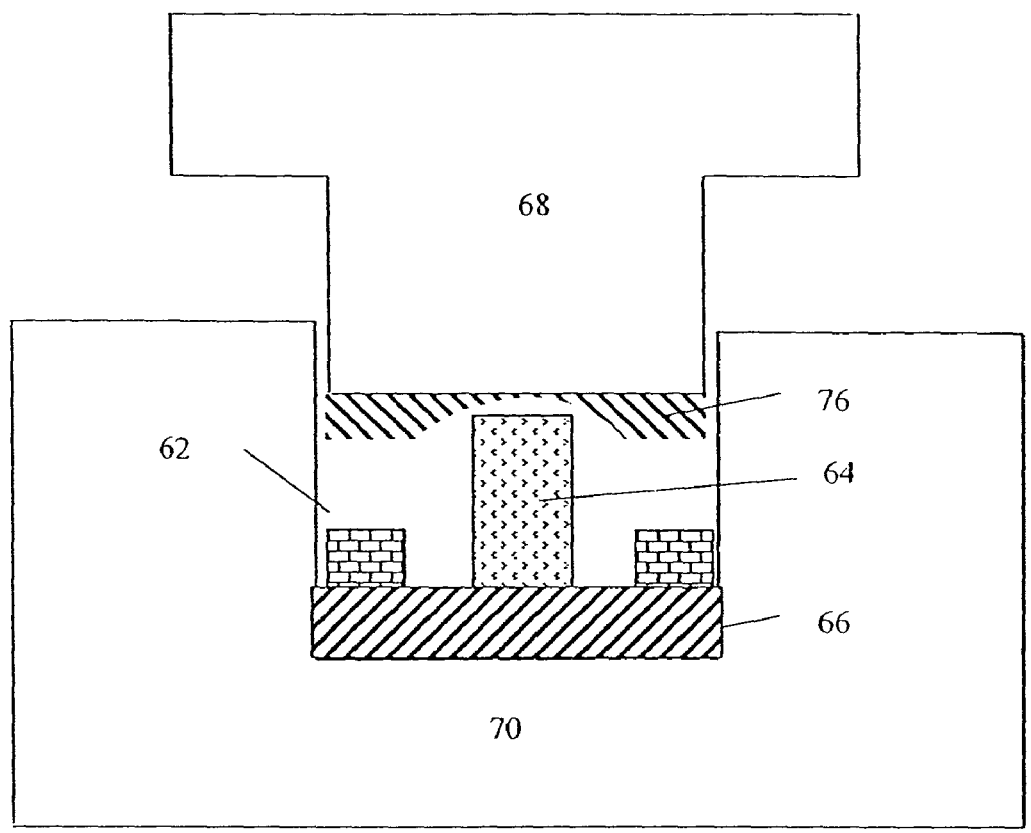
(A) Press Forging inside a split die
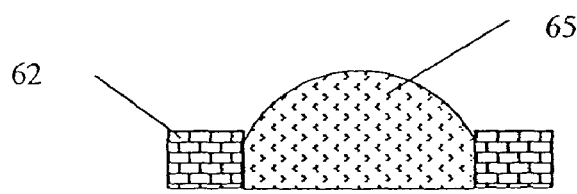
(B) Press Forged Optical Element (e.g. plano-convex lens) mounted in a split die. The elements of the die are separated from the lens after the forging process
FIGURE 8

Step I: Pressing
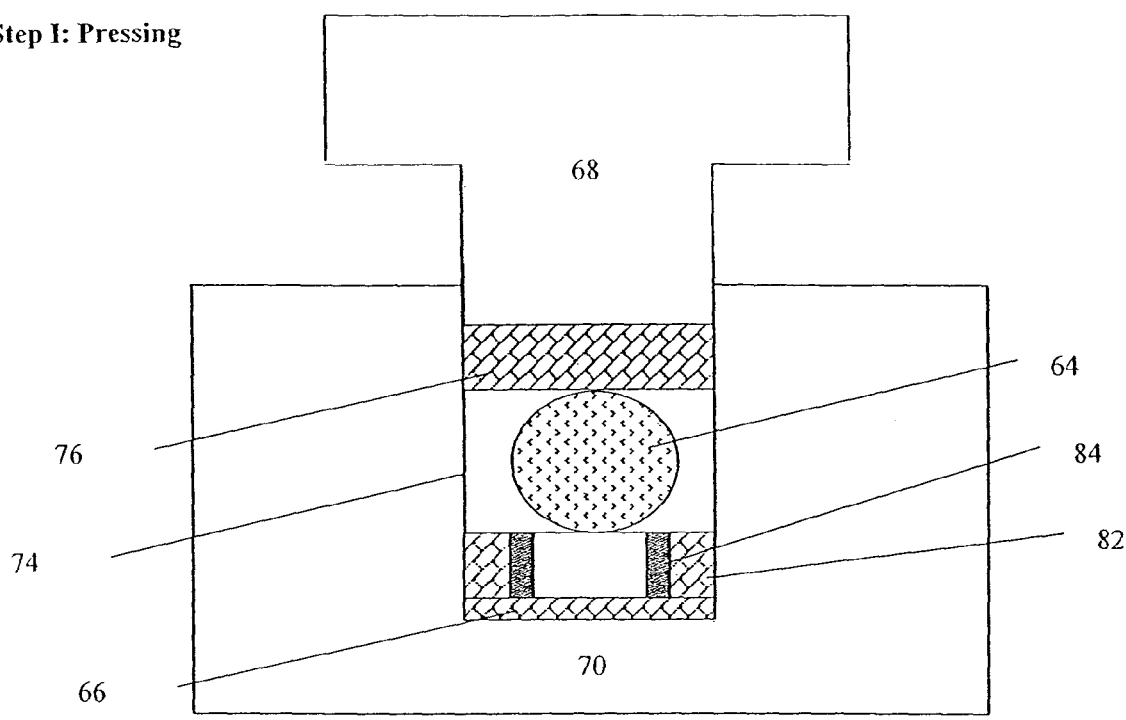
Step II: Take out holder with segments of split die and a pressed element
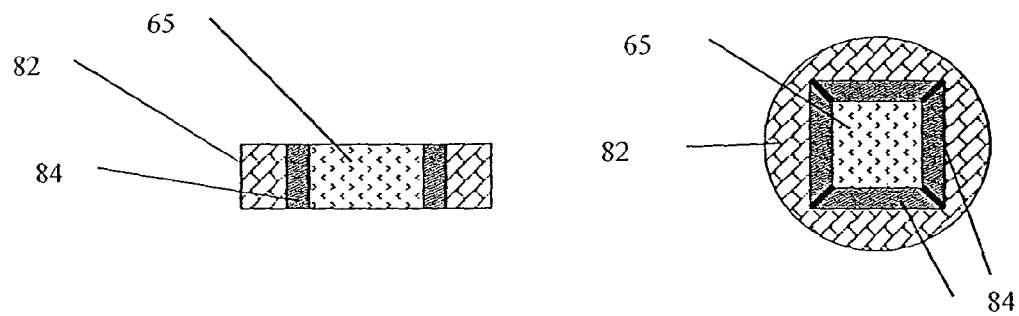
Step III: Separate the die segments and free the pressed element
Final product: press formed element 65
FIGURE 9

PRESS FORGING MULTIPLE ELEMENTS SIMULTANEOUSLY INSIDE SPLIT DIES

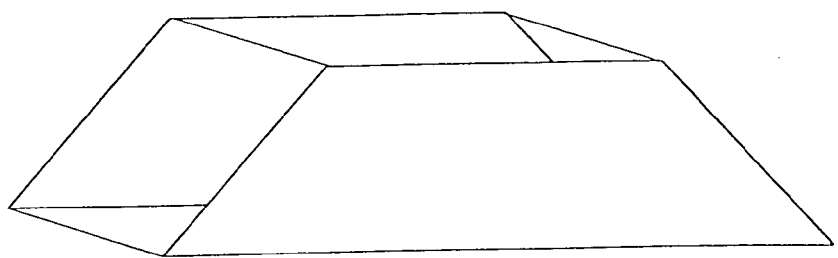
FIGURE 12A  DOVE PRISM
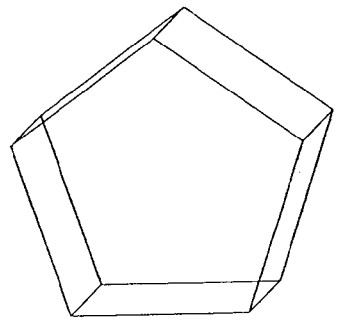
FIGURE 12B  PENTA PRISM
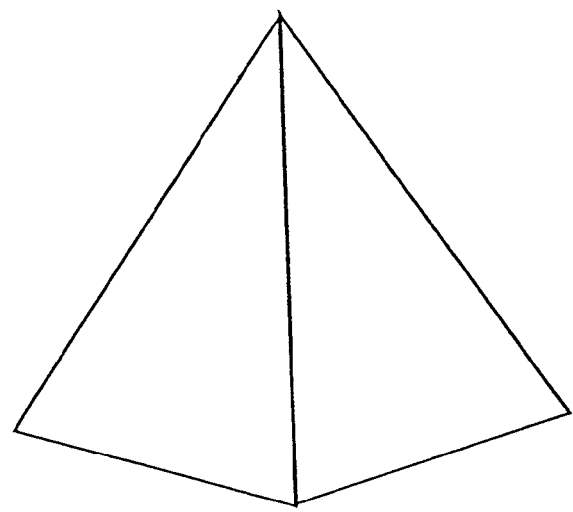
FIGURE 12C  PYRAMID
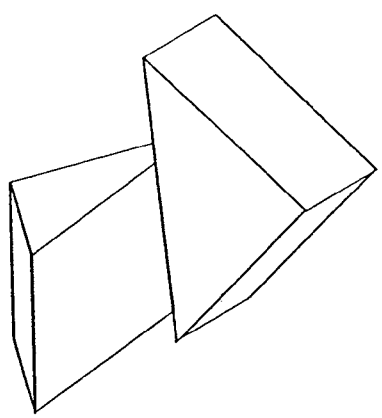
FIGURE 12D  PORRO PRISM

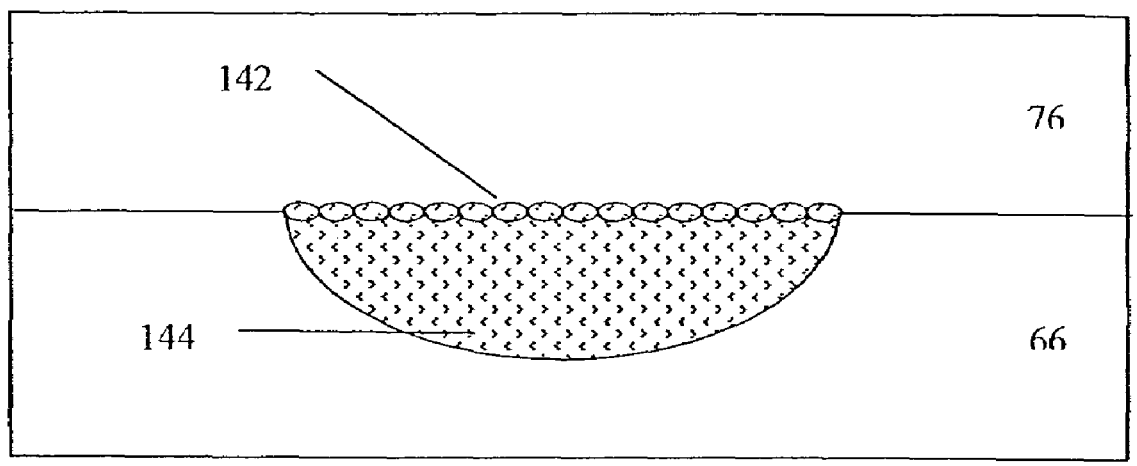
FIGURE 17  Forge Pressing a Hybrid Element

FLAT WAVEGUIDE

Tapered Flat Waveguide

FEWS Absorption Cell

FORMING TRANSPARENT CRYSTALLINE ELEMENTS BY COLD WORKING

This is a Continuation-in-Part of U.S. patent application Ser. No. 10/138,581 filed May 6, 2002, now abandoned, which is a Continuation of U.S. patent application Ser. No. 09/458,688 filed Dec. 10, 1999, now abandoned, which is based on U.S. Provisional Application No. 60/111,929 filed Dec. 11, 1998.

FIELD AND BACKGROUND OF THE INVENTION

The present invention relates to the preparation of optical elements by cold working of formable (i.e. ductile) crystals. More specifically, the present invention relates to the preparation of elements for infrared applications, using processes such as cold forging, embossing, or stamping, which are carried out in a narrow temperature range, using a sacrificial split die. The present invention also relates to the use of such elements, and in particular of thin waveguides, as the bases for a system that can be applied for the diagnosis of tissues or biological fluids, in medicine. The same diagnostic system could be used in cosmetics for skin analysis or for the measurement of the diffusion of medical drugs or cosmetics into the skin.

Infrared (IR) radiation covers a wide spectral range which can be divided into three ranges: NIR=near IR ($\lambda$=1 µm-3 µm); MIR=middle IR (e.g. $\lambda$=3 µm-30 µm) and FIR=far infrared ($\lambda$=30 µm-100 µm). There are several scientific, industrial, medical and military applications that make use of infrared radiation and in particular of MIR radiation. Among these applications are the following:

IR detection: A warm body at a temperature T emits radiation ("black body" radiation") whose intensity I is given by the formula: $I=\epsilon\sigma T^4$ where $\epsilon$ & $\sigma$ are constants. For bodies near room temperature most of this emission is in the MIR range, and suitable IR detectors can measure 1. The measurement of this radiation serves for military applications such as detection of personnel or vehicles in total darkness. It also serves scientific and medical applications such as non-contact determination of the surface temperature T.

Thermal Imaging: The distribution of intensities emitted from a large area can be determined by a large array of IR detectors and displayed on a monitor. This has been used mostly for military applications (e.g. FLIR), because the arrays used were very expensive. A new generation of inexpensive arrays will probably be used for medical and industrial applications.

IR Lasers: Numerous lasers emit IR radiation, including solid-state lasers, such as Nd: YAG ($\lambda$=1.06 µm) or Er: YAG ($\lambda$=2.96 µm) and gas lasers, such as $CO_2$ ($\lambda$=10.6 µm) or CO ($\lambda$=5.3 µm). MIR lasers have been used for military applications, such as target designators, for industrial applications, such as cutting, heating and welding of materials, and for medical applications, such as laser surgery and laser therapy.

IR Spectroscopy: There are many organic and inorganic molecules that have characteristic absorption in the MIR (called "finger print"). This absorption serves as an important tool for material analysis. The absorption of a sample can be measured using standard (grating) spectrometers or Fourier Transform Infrared (FTIR) spectrometers, or tunable laser spectrometers. The absorption spectrum is used for determining the chemical composition of the sample. This has been widely used in industry and science. IR spectroscopy is potentially useful in biology and medicine, for IR clinical chemistry, and for IR pathology.

Some authors use the term "optical" only for the visible spectral range. Herein, all the elements that are transparent in the infrared and are used in IR system are referred to as "infrared optical elements".

Optical systems that are designed for visible light, are based on standard optical elements. Most of these optical elements make use of standard materials such as silica ($SiO_2$) based glasses or transparent plastics. All these materials are completely opaque in the MIR and other families of materials have to be used in infrared systems. These include crystals such as NaCl, KBr, $BaF_2$, $MgF_2$, Ge, Se, ZnSe, ZnS, or glasses such as $As_2S_3$, $As_2Se_3$, ZrF etc. Each of these materials is transparent in a different range in the infrared. See J. A. Savage, *Infrared Optical Materials and Their Antireflection Coatings*, Adam Hilger, Bristol and Boston, 1985.

Various optical elements are prepared from the IR transparent materials. These optical elements include small and large windows, convex or concave lenses, various prisms and miniature (refractive) optical elements. Such IR elements are generally made by techniques that have been previously used for silica based glasses: a piece of material is cut to the desirable dimensions, it is ground to the rough shape and finally it is polished to generate an exact shape with high surface quality. Elements of this type are referred to herein as "bulk" elements. The fabrication processes have been adapted for each of the infrared transmitting materials mentioned above. In many of these cases the process is much more complicated than for silica, because many of the IR materials are difficult to handle: they are brittle, water soluble or toxic. In all cases the process of making IR optical elements is complicated, time consuming and expensive, especially when trying to make large optical elements.

Arrays of microlenses (lenslet arrays) that are purely refractive have been fabricated on the surface of silica-based glasses, using various techniques. In the case of glasses, a technique called reflow has been used. For glass and other materials one can use direct fabrication methods such as diamond turning, or etching through a photoresist mask. Circular, hexagonal, square and cylindrical arrays have been formed, with individual lens size of the order of tens of microns. Similar techniques have been used for infrared transmitting glasses and crystals, such as Ge, Si and ZnSe. Manufacturers of such optical elements include MEM Optical Inc. of Huntsville, Al. and Adaptive Optics Associates of Cambridge, Mass.

There are two new families of surface-relief micro-optical elements: continuous relief optical elements and binary optical elements. Such diffractive optics elements (DOE) are called planar, because their relief amplitude is normally less than 10 µm. These optical elements are designed to convert an incoming light beam into a predetermined output beam. The output beam can be focused into a point, or shaped like a cross, or a ring or any other light pattern. Diffractive optical elements are used as lenses, beam splitters, diffusers etc. Towards this goal, sets of specially designed microscopic patterns are generated on the surfaces of standard, silica based, optical elements. The techniques for generating such patterns are normally based on photolithography, a method that had been borrowed from the semiconductor industry. These techniques involve the generation of a photoresist pattern on the optical element and etching the surface of the element through the pattern by chemical etching or dry etching. The diffractive optical elements can also be made on surfaces using diamond turning or laser ablation. See, for example, J. Turunen and F. Wyrowski, *Diffractive Optics*, Akademie Verlag, 1997. Some of these processes have been adapted for the fabrication of diffractive optics IR elements, notably by the Coherent Auburn Group of Auburn Calif., but the processes are time consuming and rather expensive.

Hybrid optical elements employ at least two of the optical technologies mentioned above. For example optical elements are made with refractive and with diffractive surfaces. This combination is used to realize some specialized optical functions. One such hybrid optical element is a traditional plano-convex lens, where a diffractive element is fabricated on the plane surface.

In the visible range use has been made of highly transparent plastics such as PMMA (i.e. Lucite or Plexiglas). One of the main advantages of these plastics is that they are softer than glass and have lower melting points. It is therefore possible to mold them or to deform them at relatively low temperatures to a desirable shape. It has been found that it is possible to prepare in this fashion molded optical elements of high optical quality and very low cost. A mold, in which the cavity is formed by two or more components held together, is called a split cavity mold. In this case, after molding, the components of the mold are separated from the molded piece at the end of the molding process. This permits to form undercuts in the molded piece. These components are re-used for molding a new batch of optical elements.

These methods lend themselves easily to mass production. Such molding procedures can easily replicate a "master" and they serve in a plethora of domestic, industrial, scientific and military applications. Replication techniques have been also used for the fabrication of refractive microlens arrays from PMMA or polystyrene, for applications in the visible.

Diffractive or binary optical elements and purely refractive micro-optical elements have been mass-produced in large quantities by replication techniques. This involves the transfer of surface relief profile from a "master" surface into formable material, such as polymer. Hot embossing was used, for example, for the fabrication of Fresnel microlenses and lenslet arrays. Injection molding was used for the fabrication of micro optical lenses and for compact discs, and casting—for spectroscopic gratings. These methods can be used for replicating any surface relief microstructure with very high resolution, at an extremely low cost. Such elements are available, for example, from Digital Optics Corporation of Charlotte, N.C., and from Lasiris of St. Laurent, Quebec, Canada.

Similar molding or replication techniques have not yet been applied for optical materials transmitting in the mid IR. In metallurgy there are four basic metal forming processes: casting, machining, consolidating of smaller pieces and deformation. Within the metal deformation processes, cold working includes the processes that change the shape and form of the metal, when the metal is at a temperature below its softening temperature. The cold working processes include press forming or stamping, rolling, extrusion, drawing and forging. In some of these, which we may define as "bulk" forming, a metal ingot is pressed between two opposing dies, or between a punch and a die, and its bulk shape is changed. Forging, for example, can be carried out in open dies or in closed dies (also called closed impression dies.) The closed die can be made of several components, and it is then called segmented die or split die. In this case the segments can be separated from the forged element at the end of the forging process. This is very similar to the split cavity mold used for plastics, as mentioned above. In other "bulk" processes the metal is squeezed between rollers or extruded through an open die to form wires, tubes etc. There are cold work processes that may be defined as "surface" forming. For example in a stamping process, the stamp has a raised pattern cut on it and when it is pressed against a metal blank it generates a design on the surface of the blank. All these cold working processes are less expensive, the sizes of the parts are more accurate and the surface finish is much better than in hot processes.

Cold working processes cause, in general, hardening of the prepared bodies, which is frequently advantageous in metallurgy. If the extra hardening is undesirable, annealing at elevated temperatures can soften the bodies. Some cold working processes, such as extruding and rolling, are carried out in multiple steps. It often is desirable to soften the work piece between steps by annealing the work piece.

It would be highly desirable to be able to use some of these well-established methods for the shaping of blanks of infrared transmitting materials into optical elements, such as lenses or windows, or modifying the surface of infrared elements to form diffractive optical elements or arrays of refractive microlenses. It is bound to reduce the time and the cost of making these elements. This would be of particular interest in the case of optically transparent crystalline materials whose handling is difficult and time consuming (especially for large elements). Unfortunately almost all of these crystals are hard and brittle and much less ductile than metals and it is difficult to deform them without fracture.

During the last thirty years there have been attempts to apply pressure to single crystals and press forge or extrude infrared optical elements. These elements are polycrystalline and after pressing they should have the same density and the same optical characteristics as the starting material. Hot press forging was applied mostly to alkali metal halides and alkaline earth metal halides, which are frangible and tend to cleave. Both uniaxial and hydrostatic press forging were tried. The temperature used in these experiments was relatively high, on the order of 500° C. This temperature was lower than the melting point $T_{mp}$ but higher than ½ $T_{mp}$ (U.S. Pat. Nos. 3,933,970; 4,089,937; 4,171,400 and 4,522,865). Similar crystals have also been extruded to form desirable shapes (U.S. Pat. No. 4,839,090). There have also been attempts to apply high temperatures and pressures to compress powders of the same materials and form infrared elements (U.S. Pat. Nos. 4,013,796, 5,643,505 and 5,658,504). Finally, infrared transmitting chalcogenide glasses were prepared by molding at temperatures higher than the melting point of the glass (U.S. Pat. No. 5,346,523). Apparently there are technical hurdles that have not yet been surmounted. Inexpensive, mass produced, infrared elements made of any of the materials mentioned above are not available in large quantities.

There are very few infrared transmitting crystalline materials that are relatively soft and ductile. The hardness of materials can be conveniently measured by the Knoop method. For ductility, one may apply stress on a sample of length A and measure the length B when the sample fractures. The value (B−A)/A, the elongation ratio, is a measure of the ductility. The elongation ratio of metals is often as high as 50%. A small number of crystalline halides such as thallium halides (e.g. TlClBr) or silver halides (e.g. AgClBr) have Knoop Hardness values of 10-20 and their elongation ratio is similar to that of metals unlike that of brittle crystals such as alkali halides. The mechanical and the photographic properties of silver halides have been studied for more than fifty years. Silver halides "flow under pressure" and have been called: "transparent metals." The studies included mechanical deformation, yield stress measurements and research on strain ageing. See, for example, M. T. Sprackling and H. Shalitt, "Strain ageing in silver chloride: II The effect of temperature on the representative curve", *Philosophical Magazine*, Vol. 48, pp. 383394, 1984. Almost all these works reported measurements on single crystals of AgCl and were carried out under tension.

Cold working methods have already applied to form three types of element from halide crystals:

I. Rolled Sheets: Some companies (e.g. the former Crystal Division of Harshaw Chemical Co., Solon Ohio, now Bicron Crystal Products of Washougal WA) have used hot—rolling techniques to prepare sheets of AgCl and AgBr of thickness of a few mm. These sheets contained various impurities with a total concentration of 40-50 ppm (see for example L. C. Towle, "Shear Strength of Silver Chloride", *J. Applied Physics*, Vol. 37, pp. 4475-6, 1966) and they were photosensitive.

II. Extruded Optical Fibers: IR transmitting optical fibers have been fabricated from silver halide or thallium halide crystals by an extrusion through an orifice of diameter 0.5-0.9 mm at temperatures between room temperature and 200° C. There are more than fifty patents discussing different fiber structures or extrusion techniques (see for example U.S. Pat. Nos. 4,188,089, 4,253,731, 4,315,667, 4,504,298, 4,721,360, 4,828,354, 4,865,418, 4,955,689, 5,575,960 and 5,602,947). IR transmitting fibers are manufactured by Oxford Electronics Ltd., Oxfordshire, UK, by CeramOptec GmbH, Bonn, Germany and by Art Photonics, Berlin, Germany. The optical transmission of these fibers is still not satisfactory, and they are not widely used.

III. Press Forged Lenses: There are more than ten Japanese patent applications that were published between 1984 and 1994 and which describe the pressing of silver halide or thallium halide crystals between two lens shaped dies, to form lenses. The forging is done at pressures of 5-10 Ton/cm$^2$ and at temperatures 200-300° C. (Japanese published patent applications: 59-212801; 04-170501; 04-340501; 04340502; 05-139764; 06-011604). None of these lenses is available commercially, and they have not been discussed in the scientific literature.

Summarizing this prior art, one may conclude that the three methods mentioned above cannot be used for mass production of infrared transmitting optical elements of high quality. The rolling technique described in (I) can be used only for making thin flat sheets, and the optical quality of the sheets obtained was rather poor. The extrusion of crystals through open dies described in (II) is a unique method for making fibers, and it is totally unrelated to the fabrication of optical elements such as windows or lenses. The press forging process mentioned in (III) describes a method for making lenses. In extensive work done by us, we discovered great disadvantages of this forging method. When one tries to forge elements at relatively low temperature (below 120° C.) the lenses crack. When one tries to forge elements at relatively high temperature (above 180° C.) there appears a chemical interaction between the crystals and the walls of the pressure chamber. This causes two problems: (i) the optical elements darken and their transmission is very poor. (ii) the walls of the chamber gradually deteriorate and become useless. It is possible to protect the top and bottom pressure plates by a thin layer of carbon or non-reactive metal, but it is not possible to protect the sidewalls. It is not practical to replace the very expensive pressure chamber after every forging procedure. This is probably why infrared lenses are not made today by forging.

In addition, there were several problems that interfered with previous studies:

(1) almost all these studies referred to single crystals or polycrystalline samples of AgCl or AgBr and not to alloys, such as AgClBr; (2) in most cases, the samples contained impurities in concentrations higher than 10 ppm; (3) most of the samples were photosensitive: they darkened under UV or visible light. All these ductile halide crystals are potentially suited for the fabrication of a plethora of infrared elements by the well-established metallurgical cold working methods. They have not been widely used, only because of the severe problems mentioned above.

The present invention addresses two issues: (a) the fabrication of infrared optical elements by metallurgical methods, using a novel method based on sacrificial dies. (b) The use of these elements in the various infrared systems, for infrared detection, thermal imaging, power transmission and infrared spectroscopy. Particularly in the case of silver halides, the present invention focuses on four major points: (I) the use of alloys of $AgCl_xBr_{1-x}$ with mechanical properties that are superior to those of AgCl or AgBr; and (II) the use of ultra pure materials, with total concentration of impurities lower than 10 ppm, to prevent the problem of darkening of the samples. (III) The use of a sacrificial split die, instead of using a simple pressure chamber. The segments of the die are separated from the optical element at the end of the process and they are discarded. (IV) Forge pressing at a well defined temperature range 120-180° C. As mentioned, forge pressing at lower temperatures gives rise to cracks in the optical elements (especially in the case of large elements), and forge pressing at higher temperature gives rise to darkening.

Attenuated total reflection (ATR) spectroscopy, also known as evanescent wave spectroscopy (EWS), has been used during the last few decades for the study of pastes, liquids and powders, in which intense scattering or absorption precludes the transmission of a probe beam. When light is totally internally reflected in prisms or waveguides, which are placed in vacuum, there is an evanescent wave, which decays exponentially outside the waveguide over a distance of a few wavelengths. In vacuum, this is not accompanied by any energy absorption. On the other hand, if instead of vacuum, the waveguide is immersed in a liquid or in another substance, the evanescent wave may be partially or totally absorbed and the transmission through the waveguide is reduced. This will predominantly occur at those wavelengths that correspond to the absorption spectrum of the sample. The spectrum of the transmission losses is the basis of ATR spectroscopy and the prism or waveguide in contact with the sample are called ATR elements.

A system for ATR spectroscopy includes three basic parts: a tunable IR source, an IR detector and an ATR element. In the MIR spectral range 3-30 μm, the commonly used light sources are a heated black body with a variable filter or a tunable diode laser. Some of the infrared detectors operate at room temperature (e.g. pyroelectric detectors) and others—at 77° K (e.g. HgCdTe detectors). The black body IR source and the IR detector may also be part of a Fourier Transform Infrared (FTIR) spectrometer. A standard ATR spectroscopy system is schematically shown in FIG. 1. The standard "bulk" ATR element is a thick waveguide with two beveled ends. IR radiation from a tunable IR source is totally internally reflected inside the waveguide. The radiation propagates until it reaches an IR detector. The sample may be in contact with one or two broader surfaces of the waveguide.

The standard ATR elements are made of materials that are highly transparent in the MIR, and they include single crystals of ZnSe, ZnS, Ge and diamond. There are some basic shapes of the elements that have been commonly used and that may be called "bulk" ATR elements. Some of these elements are thick (>3 mm) waveguides, in which there are multiple internal reflections. These include flat crystals with beveled ends, or cylindrical rods with pointed ends. There are other "bulk" ATR elements that are not waveguides, but shaped like pyramids, pointed prisms, spherical surfaces etc. In many cases it is required to couple the light into the elements using a special arrangement of flat or of spherical mirrors. Several of the commonly used ATR elements are shown in FIG. 2. FIG. 2A shows a cross section of half a sphere (or half a cylinder) 10 whose flat surface 12 is contacted with a sample. FIG. 2B shows a cross section of a pyramid (or a prism) 14, whose flat surface 16 is contacted with a sample. FIG. 2C shows a cross section of a pyramid (or a prism) 18 whose pointed end 20 is contacted with a miniature sample area. FIG. 2D shows a diamond shaped ATR element 22. FIG. 2E shows a cross section of a thick waveguide (or a cylindrical rod) 24 with two pointed ends 26. FIG. 2F shows a cross section of a thick waveguide (or a cylindrical rod) 28 with one flat end 30 and one pointed end 32. Also shown in FIGS. 2A, 2B, 2C, 2E and 2F are illustrative ray paths 34.

ATR spectroscopy has been widely used for the study of IR spectra of samples, which are not easy to measure by conventional transmission techniques. It has been used, for example, for measuring solutes in solutions, for the analysis of drilling fluids and the deterioration of engine oil, for measuring kerosene in oil shale, for determining the energy content of hydrocarbon fuel, and for chemical analysis of materials. It has also been used for determining compositional changes in materials, for surface analysis of silicon wafers, for measuring the ingredients of beer or dairy products, for determining the concentration of various substances in blood on the skin, and for measuring minute amounts of organic pollutants in water. (U.S. Pat. Nos. 3,902,807, 4,321,465, 4,553,032, 5,049,742, 5,252,829, 5,362,445 and 5,452,083).

In most cases a broad surface of the "bulk" ATR element is in contact with the sample. But, there are cases where the tip of the pointed part of a cylindrical rod or a pyramid is placed in contact with a small area on a sample. This could be used for ATR spectroscopy of microscopic samples or areas.

The original "bulk" ATR elements mentioned above were based on large segments of single crystals, such as thick plates or rods or pyramids, that had been cut, ground and polished to a desired shape (U.S. Pat. Nos. 4,595,833, 4,730,882, 4,746,179, 4,988,195, 5,015,092, 5,035,504, 5,172,182, 5,200,609, 5,229,611, 5,434,411, 5,440,126, 5,459,316, and 5,703,366). These have the advantages of a large surface area contacting the sample, well established fabrication methods and ease of determining and maintaining a specific angle of incidence of illumination between the plane, parallel surfaces. However, the "bulk" elements are large, expensive and susceptible to damage, because of mechanical scratches and because of chemical interaction with the measured samples. Furthermore, these elements are not flexible and they require frequent polishing to maintain their useful qualities.

There is a need to find a way of producing "bulk" ATR elements using processes that are faster, more flexible and much cheaper. Such elements could be replaced frequently, if needed, and they will make ATR spectroscopy a more widely used method. This is a motivation to use cold working methods for the forming of ductile IR transmitting crystals. This can be applied for the preparation of "bulk" ATR elements (including thick waveguides).

With the development of new fibers that are extruded from crystals that transmit well into the mid-IR (out to about 25 µm), it was proposed by various workers to use these fibers both as IR cables and as fiberoptic ATR elements. The IR fibers can be long and flexible, so they can be bent to conform to the surface to be measured. They are also inexpensive to manufacture, and can be replaced after each measurement, if necessary. These features led to the development of Fiberoptic Evanescent Wave Spectroscopy (FEWS). In a FEWS system two long lengths of IR transmitting fibers coated with a thick plastic jacket serve as IR cables. The IR cables transmit the light from the IR source to an ATR element (bulk or fiberoptic) and from this sensing element to the IR detector. A short section of an unclad fiber may serve as an ATR element that is in contact with a sample. Such a system is shown schematically in FIG. 3 and was the topic of several patents (U.S. Pat. Nos. 4,798,954, 4,827,121, 5,525,800 and 5,585,634). FIG. 3 is a schematic illustration of a Fiberoptic Evanescent Wave Spectroscopy (FEWS) system based on two long IR cables and a sensor (ATR) element that can be a short segment of cylindrical unclad IR fiber or a thin flatwaveguide. There are cases where it is advantageous to replace the fiberoptic sensor element in FIG. 3 by a "bulk" element and this was the topic of other patents (U.S. Pat. Nos. 4,829,186, 5,170,056 and 5,440,126). The main advantage of both FEWS systems (with "bulk" or with fiberoptic sensing elements) is that they can be used to carry out spectroscopic measurements in remote locations.

It has also been suggested to use mixed silver halide IR fibers as the ATR elements. These crystalline fibers, of the general formula $AgCl_xBr_{1-x}$, with $0<x<1$, are described in S. Shalem et. al., "Mechanical and Optical Properties of Silver Halide Infrared Transmitting Fibers", *Fibers and Integrated Optics*, vol.2 no.9, pp.872-879 (1996). Fibers of diameter 0.5-1 mm and lengths up to 10 meters can be fabricated. These fibers are transparent between 0.5 and 25 µm, with a transmission loss minimum of about 0.2 dB/meter at 10 µm. Such fibers are nontoxic, non-hygroscopic and flexible.

It has been found that Fourier Transform (FTIR) FEWS systems, using these silver halide fibers as waveguides, can be used to perform measurements on a variety of samples, such as thin layers, liquids, powders and gases at various pressures. Furthermore, FEWS systems based on tunable diode lasers (TDL) or quantum cascade lasers (QCL) can be used to detect pollutants in water, which is important for environmental protection, in general, and in particular, for monitoring pollutants such as hydrocarbons or pesticides in water. The fiberoptic sensing element may be coated with a suitable plastic coating that causes enhancement of the pollutant signal. With such a coating the system can detect a few parts-per-billion of pollutants Such as chlorobenzene in water in a remote location and in real time.

However, even these cylindrical fibers are not ideal as sensing elements. While they overcome the problems of difficulty of working, they are still problematic with regard to the angle of incidence. Optimum configurations must be found since the signal-to-noise ratio increases as the fiber diameter decreases, while if the diameter is very small, it is difficult to couple light into the fiber.

One attempt to solve this problem is by tapering a central portion of a cylindrical fiber. An example is U.S. Pat. No. 5,239,176 to Foster Miller. This patent discusses tapering the optical fibers and indicates that silver halides are also suitable materials for the sensor fiber core. Very small pieces of chalcogenide glass fiber (2.5 cm long and 400 microns in diameter) were tried, but did not have adequate sensitivity. It was then discovered that reducing the diameter of a chalcogenide fiber could increase its sensitivity. This can be done by heating the fiber and pulling it to create a taper. Other attempts involved stripping the central part of a core/clad fiber and leaving the unclad section as the sensor element or bending the fiber (U.S. Pat. Nos. 5,416,579, 5,436,454 and 5,525,800). Also, the fiber sensor element was coated with various plastic coatings, either to protect it or to enhance the obtained signals (U.S. Pat. No. 4,893,894). Some of these elements are schematically shown in FIG. 4. FIG. 4A shows a short section 36 of unclad fiber. FIG. 4B shows a section 38 of clad fiber, where the cladding 40 has been removed at the center part 42, exposing an unclad section 44. FIG. 4C shows a segment of unclad fiber 46 that had been tapered: the two ends 48 have larger diameters than the central section 50. FIG. 4D shows a bent section 52 of unclad fiber 54. FIG. 4E shows a segment of unclad fiber 56 coated with a very thin protective layer 58. FIG. 4F shows a section of unclad fiber 60 coated with a layer 62 of porous polymer. Solute molecules (e.g. pollutants in water) can diffuse in, but the solvent (e.g. water) cannot. This gives rise to "enrichment" and higher detectivity.

There are, however, a number of disadvantages in the use of these tapered fibers. First, due to their cylindrical cross-section, a unique angle of incidence cannot be maintained, so calibrations and calculations are necessary when they are used. Second, chalcogenide glasses can be difficult to work with, because of their brittleness and the small area of contact between the tapered (cylindrical) sensor and the sample.

There is thus a widely recognized need for, and it would be highly advantageous to have, a thin flat waveguide which is flexible like a fiber, but which has the optical advantages of a thick plate or prism. An important issue addressed by the present invention is how to make thin waveguide ATR elements and how to couple IR radiation into and out of these waveguides.

During the last few decades optical and spectroscopic methods have been developed rapidly in the visible spectral range. Modem optical methods, making use of lasers and optical fibers, holography, and modern imaging technologies have been used in many scientific and industrial applications for diagnosis of materials, analysis of reactions etc. There has been an attempt to use very similar methods in medicine. In particular it had been expected that such methods could be used in clinical chemistry (e.g. blood analysis) or in pathology (e.g. in early diagnosis of diseases) for measurements in situ and in real time. This has proven to be much more difficult than had been anticipated. There are still severe obstacles in using modern optical methods for tissue diagnosis or blood analysis.

During the last few decades there has also been a rapid development in the field of infrared science and technology. In particular, infrared spectroscopy has been improved and the combination of new infrared detectors, modern electronic equipment and powerful computers, led to a revolution in this field. Methods such as FTIR spectroscopy are being used now in many areas in science and technology. These include the ATR methods mentioned above (U.S. Pat. Nos. 4,169,676 and 5,452,715).

There have been attempts to use IR spectroscopy in the field of medicine. One of the areas tried is IR clinical chemistry. The advantage of IR in this field is that sample preparation is easy, there is no need to use chemical reagents, and the results are obtained in real time and in situ. Biological fluids such as blood or urine or the synovial or interstitial fluids have been analyzed by spectroscopic IR measurements (including ATR measurements). The very preliminary results indicate that blood analysis can be done by these techniques. A second area where IR spectroscopy could be very useful is IR pathology. Various tissues have been analyzed, such as diseased and healthy tissues in the case of Alzheimer disease, plaque and healthy artery walls in cardiology etc. One of the most important tissues to be studied is cancerous tissue, in an attempt to obtain early cancer detection. Several groups have found that the FTIR spectra of different types of cancerous tumors are different from those of healthy tissues (U.S. Pat. Nos. 5,038,039, 5,539,207 and 5,596,992). Still, IR spectroscopic methods, including FTIR—ATR spectroscopy of tissues and biological fluids, have not yet gained acceptance among physicians.

Simpler optical methods have been applied in the field of cosmetics. The interest there is in skin analyzers. In this field it is desirable to determine, for example, the water content or the fat content of the facial skin. The methods used rely on scattering of light or on determining the color of the skin, but, again, these methods are limited (U.S. Pat. Nos. 4,494, 869, 5,094,248 and 5,745,217).

It is anticipated that the uses of ATR infrared spectroscopy, using cold pressed ATR elements or thin waveguides, as sensing elements, will change the situation. Such elements would be useful for tissue diagnosis and for blood analysis, in medicine. Unlike the standard, bulky ATR elements, the pressed ATR elements, and especially the thin flattened guides, could be used for measurements inside the body. They could be inserted into the body (for example under the skin) via hypodermic needles and used for single measurements or continuous measurements. They could also be inserted into the body via standard endoscopes. These pressed ATR elements would also be useful in cosmetics for skin analysis or for the measurement of the penetration of drugs or cosmetic lotions or ointments into the skin.

SUMMARY OF THE INVENTION

According to the present invention there is provided a method of forming an optical element, including the steps of: (a) providing an ingot of an ionic crystalline material, and (b) pressing the ingot between an upper die and a lower die, while the ingot is confined laterally by a split die.

According to the present invention there is provided a method of forming a plurality of optical elements, including, for each optical element, the steps of: (a) providing a respective ingot of an ionic crystalline material; and (b) pressing the respective ingot between an upper die and a lower die while the ingot is confined laterally by a respective split die.

According to the present invention, optical elements are formed by mechanical deformation (e.g. cold working) of IR transmitting crystals that are soft and ductile (i.e. formable), at temperatures 120-180° C. These crystals are ionic, as opposed to covalent or metallic, and have Knoop hardness of at most about 20. One or more steps of mechanical deformation are used inside a sacrificial split die to form "bulk" elements such as lenses, windows, prisms, flat waveguides, non imaging optical elements or any other shaped optical element that are transparent in the IR. The starting material may be a single crystal or a polycrystalline sample, and the term "crystalline", as understood herein, refers to both single crystals and polycrystalline bodies, but the pressed elements are always polycrystalline.

Specifically, one or more crystalline ingots are pressed between an upper die and a lower die while being confined laterally by respective sacrificial split dies. The split dies are "sacrificial" in the sense that each die is used only once, to form a respective optical element from a respective ingot, and then is discarded. The split dies are inert relative to their respective ingots, meaning that the chemical interaction between the split dies and their respective ingots is negligible in the preferred temperature range of 120° C. to 180° C. Preferred materials for the split dies include titanium, tungsten, tungsten carbide and stainless steel. A split die may consist of one segment, or may consist of a plurality of segments.

In the visible spectral range there are optical elements that are actually constructed from several single elements. For example there are various combinations of prisms, such as the Porro prisms, the Abbe prism, and many others, that are used for various applications. There are also combinations of lenses, such as achromatic lenses, that consist of several lenses. According to the present invention, "compound" optical elements are fabricated in the IR, using one or more steps of mechanical deformation inside a sacrificial split die. These compound optical elements consist of a combination of several single elements, for example, compound lenses, consisting of several lenses, or combinations that are not necessarily useful in the visible, such as a lens and a prism.

According to the present invention, mechanical deformations inside a sacrificial split die are used to modify the surface of "bulk" elements and impress on these bulk elements diffractive optical elements, binary optical elements, arrays of miniature refractive optical elements, planar optical elements, or integrated optical elements.

According to a preferred embodiment of the present invention, the IR elements are formed of halide salts that are relatively soft and ductile (i.e., elongation ratio greater than about 10%), for example silver halides and thallium halides. Halides, such as AgClBr exhibit a mechanical behavior that is somewhat similar to copper. Therefore the hardness of the optical elements may be changed: they may be made harder, due to work hardening, or softer, due to an annealing process. The annealing is useful during the steps of press forming of the IR elements. The hardening generates optical elements that are much easier to use than the softer single crystals themselves.

According to another preferred embodiment of the present invention, the elements are formed of a mixed silver halide, such as the one of the formula $AgCl_xBr_yI_{1-y-x}$ where $0<x+y<1$. In most cases $0.3<x<0.7$. It should be noted that the term "silver halide", as used herein, refers to both pure silver halides, such as AgCl and AgBr, and mixed silver halides, such as $AgCl_xBr_yI_{1-y-x}$.

According to another embodiment of the present invention, IR elements are made by placing pieces of single crystals of silver halide inside sacrificial split dies and then pressing them between a top die and a bottom die (e.g. with highly polished surfaces) to form polycrystalline elements, at a temperature in the range 120-180° C. and at pressures in the range 0.1-10 tons/cm². The elements of the sacrificial split dies are then separated from the forged halide work piece and discarded. All these mechanical processes produce infrared transmitting "bulk" elements for imaging and non-imaging applications. These include flat windows, thin infrared waveguides, convex lenses, concave lenses, cylindrical lenses, aspherical lenses, prisms, etc.

According to another embodiment of the present invention, diffractive optical elements, binary optical elements, arrays of miniature refractive optical elements, such as lenses or cylinders, or arrays of diffractive elements, or integrated optical elements, are impressed on the surface of silver halide windows or lenses or prisms, using suitable stamping (e.g. male dies) or embossing. Microoptical elements impressed on relatively thick waveguides are used for the fabrication of planar optics elements. Grooves are impressed on the surface of the elements and used for inserting metal wires (e.g. for heating) or gases (e.g. for cooling).

The present invention solves the problem of using cold working for making infrared elements, without causing cracks and without causing darkening in the forged pieces. This method lends itself to mass production of inexpensive infrared elements.

According to the present invention, there is provided a simple and inexpensive way of producing both "bulk" ATR elements and thin waveguide elements for evanescent wave spectroscopy. The "bulk" elements are formed by mechanical deformation of IR transmitting crystalline materials inside a sacrificial die. Thin planar waveguides also may be formed in the same way but preferably are formed by the press forging of flexible IR fibers.

According to one preferred embodiment of the present invention, the "bulk" ATR elements are formed by cold forging of soft and ductile infrared transmitting crystals, such as silver halide of the formula $AgCl_xBr_yI_{1-x-y}$, where $0<x+y\leq1$, inside sacrificial split dies. Press forging of highly purified crystals results in ATR elements that are very similar to standard ATR elements: they are highly transparent in the infrared and their surface properties are excellent. All of the "bulk" ATR elements shown in FIG. 2 and similar ones can be fabricated in one or more steps of cold working inside sacrificial split dies. These elements include prisms, pyramids, diamond shaped elements, flat waveguides with beveled ends, cylindrical rods with flat or pointed ends, spherical and aspherical lenses, etc.

The present invention addresses one of the major problems of using ATR spectroscopy: the cost of the elements. Standard ATR elements are made of expensive single crystals which are difficult to process, and their grinding and polishing are time consuming and expensive. The present invention is based on ATR elements that can be processed quickly and cheaply by mechanical deformation, such as press forging.

Following the teachings of the present invention, a variety of such elements have been fabricated by mechanical deformation of single crystals of AgClBr. The elements are polycrystalline, and their optical and chemical properties are almost identical to those of single crystals. All these elements have been successfully tried as ATR elements in conjunction with FTIR system, or with tunable laser systems or with a system based on a hot source ("black body") and a tunable filter.

According to one preferred embodiment of the present invention, thin waveguide ATR elements are formed by mechanical deformation of a mixed silver halide crystal or fiber of the formula $AgCl_xBr_yI_{1-x-y}$, where $0<x+y\leq1$ inside sacrificial split dies According to another preferred embodiment of the present invention, the thin waveguide has a thickness of between about 0.02 and 1 mm.

Further, according to another preferred embodiment of the present invention, the plate merges into ends of greater thickness, for coupling in light. The present invention successfully addresses the shortcomings of the presently known fiberoptic configurations by providing a flat optical waveguide which is inexpensive to manufacture, which can be formed to any desired length, which has a relatively large surface area contacting the sample, which is sufficiently flexible to conform to a wide variety of samples and which provides straightforward and accurate measurements of attenuated total reflection. In particular, use of these waveguides does not require complex calculations of angle of incidence and so forth. It has been shown both theoretically and experimentally that the use of thin waveguides will tremendously increase the sensitivity of diagnostic systems.

As mentioned above, one of the important areas of applications of the ATR elements discussed above is in biology and medicine. Pressed ATR elements are used in contact with the skin, placed subcutaneously, under the skin, inserted into various tissues via hypodermic needles or catheters, or inserted via endoscopes and placed in contact with tissues. They even can be used for continuous monitoring of tissues.

The use of these elements has been demonstrated in the following applications:

IR Clinical Chemistry and Blood Analysis

When the ATR element is in contact with blood, one can measure the absorption, which is rather similar to that of water. By using various chemometry methods, such as multivariate analysis or neural network analysis, we have been able to correlate the absorption signals with the concentrations of important constituents of blood, such as glucose, cholesterol, proteins, uric acid etc. Similar methods can be used for the analysis of other biological fluids such as urine, interstitial fluids, synovial fluid, tears etc.

IR Pathology and Cancer Detection

The absorption signal obtained for healthy tissue is different than the one obtained for diseased tissue. For example, we found in animal experiments that the absorption signal for cancerous tumor is different than the one obtained in neighboring healthy tissues. We have been able to demonstrate this effect in urinary tumors and in skin tumors. In early clinical experiments we observed differences between healthy areas on human skin and diseased areas on the skin.

Skin Analysis and Cosmetics

We placed on the skin various lotions such as medical drugs or sunscreen lotions. Each of these has a characteristic infrared absorption. By placing an ATR element on the skin we determined the constants of diffusion of these materials into the skin.

Also, with ATR spectroscopy we determined the water content of the skin.

In all the above-mentioned applications, it is advantageous to use ATR elements that are fabricated by cold working, because of their low cost. These could be part of a regular infrared spectrometer or part of a FEWS system. If high sensitivity is desirable, then the thin flat waveguides discussed above and tunable IR lasers should be used.

BRIEF DESCRIPTION OF THE DRAWINGS

The invention is herein described, by way of example only, with reference to the accompanying drawings, wherein:

FIG. 5 is a schematic diagram of a prior art system, for press forging of windows or lenses, in which the crystal is pressed by a piston and a top die against a bottom die, inside a pressure chamber;

FIG. 6 is a schematic diagram of a prior art system, for extrusion of IR fibers, in which a punch presses the crystal through an open die;

FIG. 7 is a schematic diagram of a system of the present invention for forging a forgeable crystal inside a sacrificial split die, specifically, for forge pressing a window inside a split ring, using top and bottom flat dies;

FIG. 8 is a schematic drawing of the system of the present invention being used for forge pressing a lens inside a ring shaped sacrificial split die;

FIG. 9 is a schematic drawing of the system of the present invention being used for forge pressing a square shaped window inside a square shaped sacrificial split die;

FIG. 12 shows various "bulk" elements that may be formed by forge pressing forgeable crystals inside sacrificial split dies;

FIG. 17 illustrates cold working methods inside sacrificial split dies, as applied to the fabrication of "hybrid" elements, which combine bulk, and surface elements;

DESCRIPTION OF THE PREFERRED EMBODIMENTS

Figure 1:
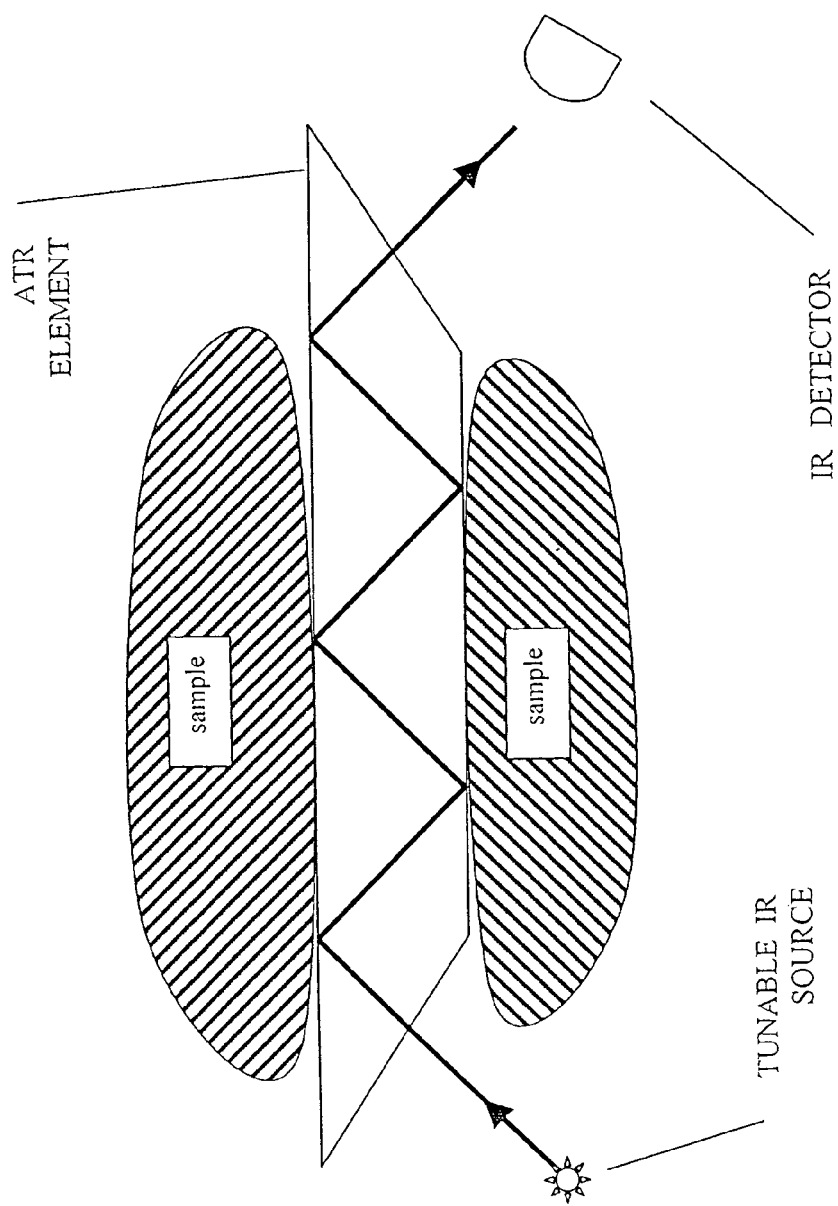
FIG. 1 is a schematic diagram of a prior art ATR spectroscopy system.
Figure 2A:
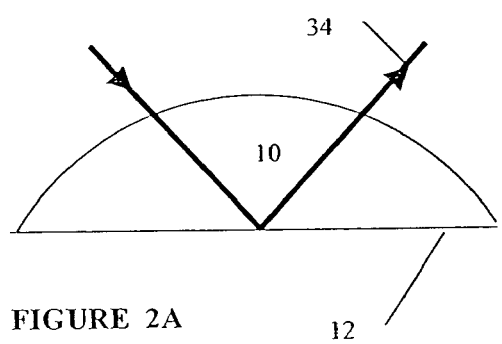
FIG. 2 shows six commonly used ATR elements.
Figure 2B:
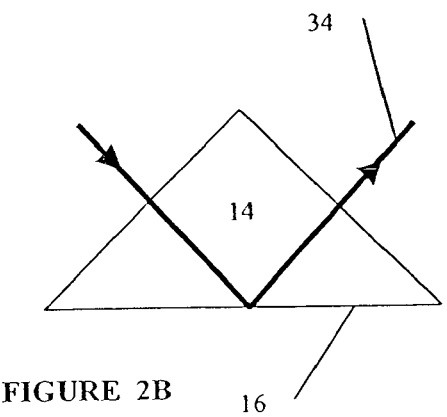
Figure 2C:
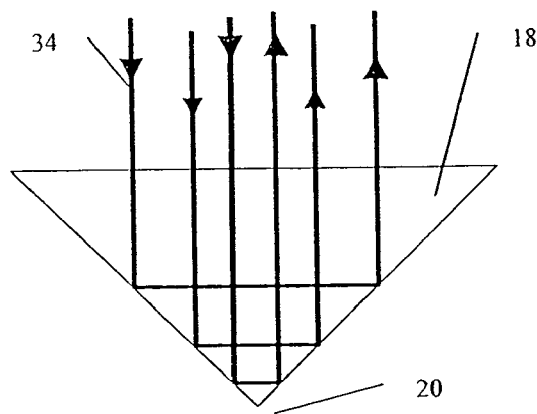
Figure 2D:
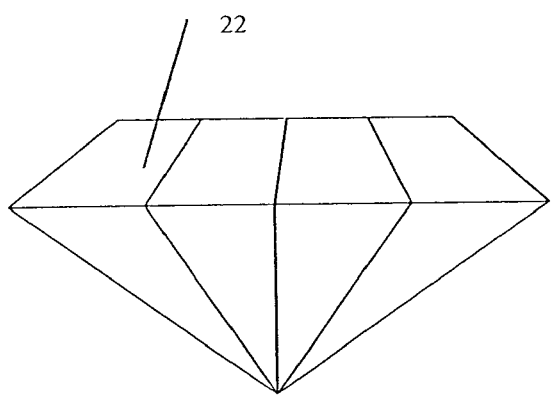
Figure 2E:
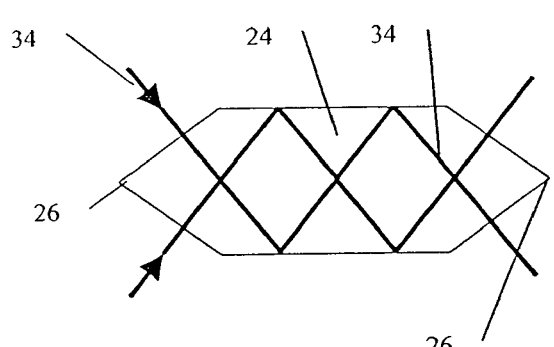
Figure 2F:
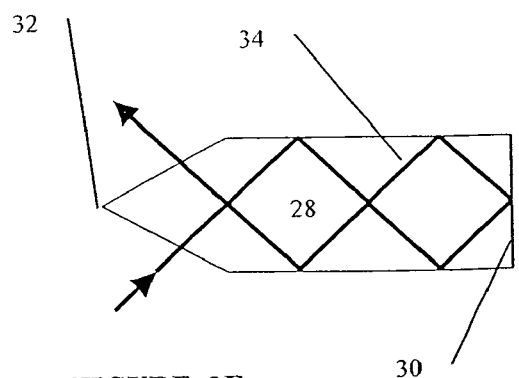

The present invention is of a method of preparing a monocrystalline or polycrystalline ingot of a soft and ductile IR-transmissive material and cold working the ingot to produce polycrystalline elements of desired shapes. Specifically, the present invention can be used to make optical elements for ATR infrared spectroscopy.

The principles and operation of producing IR optical elements according to the present invention may be better understood with reference to the drawings and the accompanying description.

The mechanical methods used in the present invention are similar to the cold working methods used in metallurgy. These include press forging for the fabrication of "bulk" optical elements and stamping, or coining, or embossing, for the fabrication of "surface" optical elements.

The preferred starting material is a large crystal that is highly transparent in the mid-infrared and is ductile. The crystal is of very high purity, and with minimum scattering. The reduction in the number of impurities is needed to obtain high transmission in the mid-infrared and to reduce darkening under exposure to visible light or to ultraviolet light. Smaller ingots cut from the large crystal are used for cold working. These ingots are placed between highly polished dies or between a punch and a die and are pressed. These die are made of a metal that does not interact with the crystal under high pressure and at elevated temperatures (for example titanium or high quality stainless steel). Or it may be coated with a layer of material that does not interact with the crystal (for example WC). The ingots are forge pressed inside sacrificial split dies, and the segments of these dies are separated after the process, and discarded. The split dies are also made of titanium or tungsten carbide or any other hard material that does not interact with silver halides. The segments of the split die could be simply held by the pressure chamber, as shown in FIG. 7 below. Alternatively they could be held by a holder, which is made of a hard material (e.g. steel), which may interact with silver halide, as shown in FIG. 9 below. This holder is not brought in contact with the ingot and it is also discarded. Because each sacrificial split die is used only once, for one ingot, the sacrificial split dies are referred to herein as "respective" sacrificial split dies of the optical elements being formed. The use of split dies prevents interaction with the walls of the pressure chamber. The forge pressing is done at a well-defined temperature range that is sufficiently high to prevent cracking of the workpieces, and that is sufficiently low to prevent darkening of the forged elements.

Referring again to the drawings, FIG. 5 illustrates a prior art method of cold working of infrared elements. A monocrystalline ingot 64 is pressed between two flat dies 76 & 66, by a piston 68 moving vertically downward into a base 70. The optical quality of dies 76 & 66 determines the surface quality of the resulting element 65. FIG. 6 illustrates a prior art method for extruding an optical fiber. An ingot 64 is extruded through a lower die 72 by the vertically downward motion of a piston 68 (i.e. punch) into a base 80. The cross section of the pressed or extruded fiber 75 is much smaller than that of ingot 64. The optical quality of the die 72 determines the surface quality of fiber 75. Alternatively the starting material could be a polycrystalline sample that had been previously press forged from a single crystal.

FIG. 7 illustrates the fabrication of a circular flat window inside a sacrificial split die according to the present invention. In FIG. 7A, piston 68 presses ingot 64 between two flat dies: a top die 76, and a bottom die 66 that is placed on the bottom 70 of the pressure chamber. The ingot is pressed inside a ring shaped die 63, which may consist of three segments 62, as shown in FIG. 7B. The split ring 63 may also consist of just one segment, as shown in FIG. 7C. During the process the forge pressed ingot forms a pressed window 65, which never comes to contact with the walls 74 of the pressure chamber. At the end of the process the three segments 62 shown in FIG. 7B are separated from the window and are discarded. In the configuration shown in FIG. 7C, the split ring is pushed open, at the end of the process, by inserting some object into the slit in the ring, and the press forged object is removed. In this case the ring could be made of a elastic material (e.g. stainless steel).

FIG. 8 illustrates the fabrication of a lens inside a sacrificial split die. The whole process is identical to that described in FIG. 7, except that the top die 76 is curved. The top surface of the forge pressed ingot is therefore a curved surface of a lens, whereas the bottom surface is flat.

Figure 10:
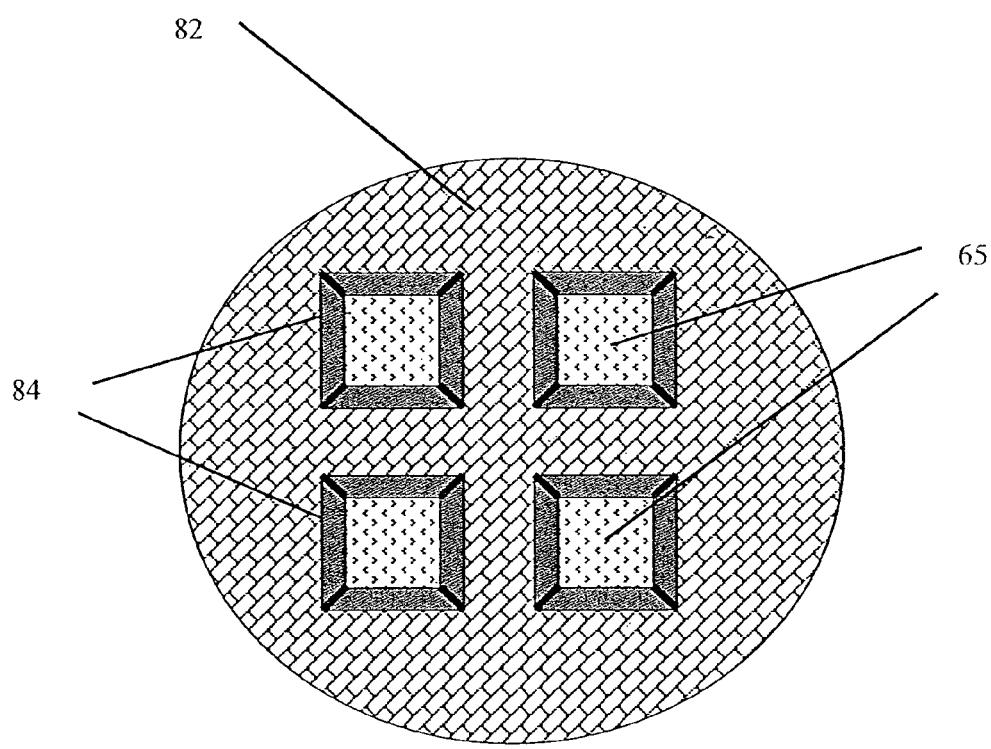
FIG. 10 is a schematic drawing of the system of the present invention being used for simultaneous forge pressing of four square windows inside four respective sacrificial split dies.

FIG. 9 illustrates the fabrication of a flat window in a sacrificial split die that is mounted inside a holder. Piston 68 presses ingot 64 between a top die 76 and a bottom die 66. The split die 63 consists of four straight segments 84 that are made of Ti or WC and they are held inside a holder 82 made of some hard steel. Ingot 64 is forge pressed inside this split die 63, and again ingot 64 never comes in contact with the walls 74 of the pressure chamber. At the end of the process the segments 84 of the die 63 are discarded, leaving a stand-alone window 65 FIG. 10 illustrates the simultaneous fabrication of four windows 65 by press forging. The process is identical to that described in FIG. 9, but in this case four sacrificial split dies 63 are used.

FIGS. 7-9 illustrate sequential press forging of optical elements 65. Each optical element 65 is press forged while being laterally confined by a respective split die 63 that is then discarded and not used for the press forging of any other optical element 65. FIG. 10 illustrates the simultaneous press forging of a plurality of optical elements 65.

FIG. 11 illustrates some of the "bulk" infrared elements that can be fabricated by press forging. Ingot 64 is pressed between opposed surfaces of dies 76 & 66 at a temperature between 120° C. and 180° C., while being confined laterally by a sacrificial split die. When sufficient pressure is applied, ingot 64 is transformed into a homogeneous, polycrystalline element 65. FIG. 11A shows element 65 as a window or flat waveguide. FIG. 11B shows element 65 as a prism or a pyramid. FIG. 11C shows element 65 as a concave lens. FIG. 11D shows element 65 as a cylindrical or spherical lens. FIG. 11E shows element 65 as a convex element. FIG. 1F shows element 65 as a convex lens. FIG. 1G shows element 65 as an aspherical element. Element 65 of FIG. 1G is actually a "compound" element that is constructed of two halves that are pressed or extruded together. FIG. 11H shows element 65 as an aspherical lens.

FIG. 12 illustrates, in perspective view, various prisms that can be fabricated by press forging or by extrusion. FIG. 12A shows a dove prism, a prism with parallel faces and beveled ends. FIG. 12B shows a pentaprism. FIG. 12C shows a pyramid. FIG. 12D shows a Porro prism. A Porro prism is a "compound" prism, constructed of two right angle prisms, used for erecting and displacing an image.

Figure 13A:
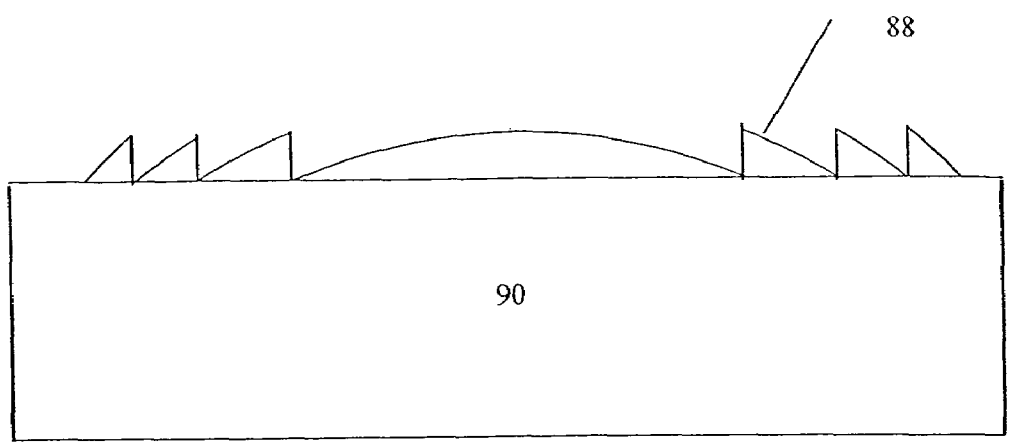
FIG. 13 shows Fresnel lenses that can be formed by stamping or embossing, using the forging system of the present invention.
Figure 13B:
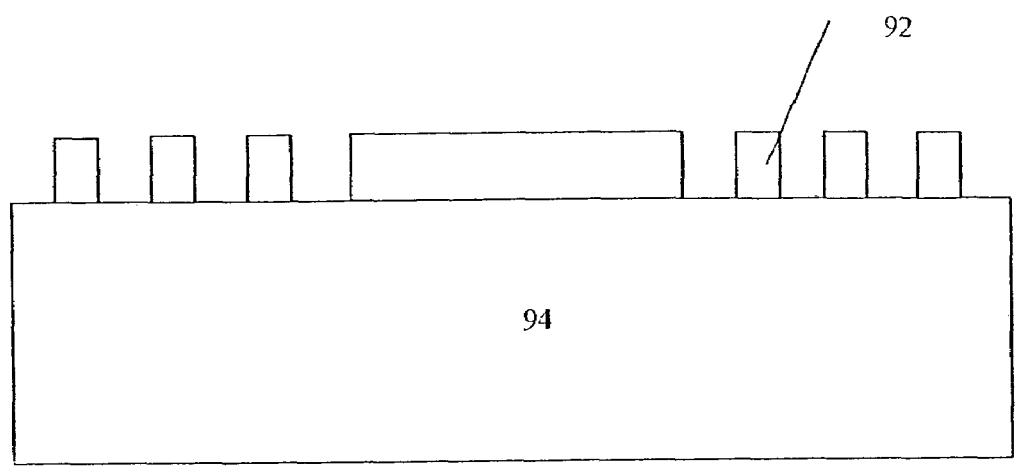
Figure 13C:
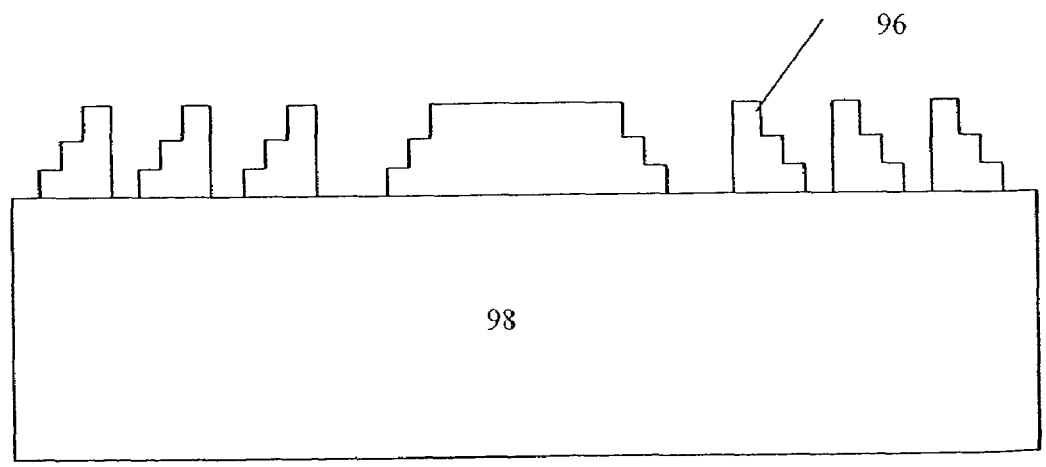

FIG. 13 illustrates, in cross section, some diffractive elements that can be formed by stamping or embossing on the surface of a single crystal element or on a polycrystalline "bulk" element. FIG. 13A shows a continuous relief Fresnel lens 88 embossed on the top surface of a bulk element 90. FIGS. 13B and 13C illustrate binary optical elements. FIG.

13B illustrates a one level Fresnel lens 92 embossed on the top surface of a bulk element 94. FIG. 13C shows a three level Fresnel lens 96 embossed on the top surface of a bulk element 98.

Figure 14A:
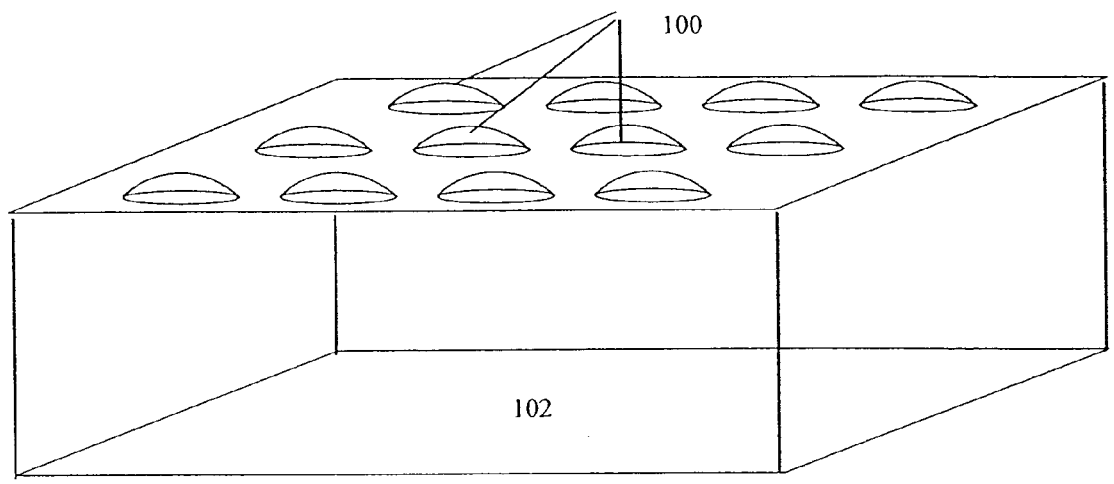
FIG. 14 illustrates arrays of miniature refractive elements formed by stamping on the surface of an infrared element, using the system of the present invention.
Figure 14B:
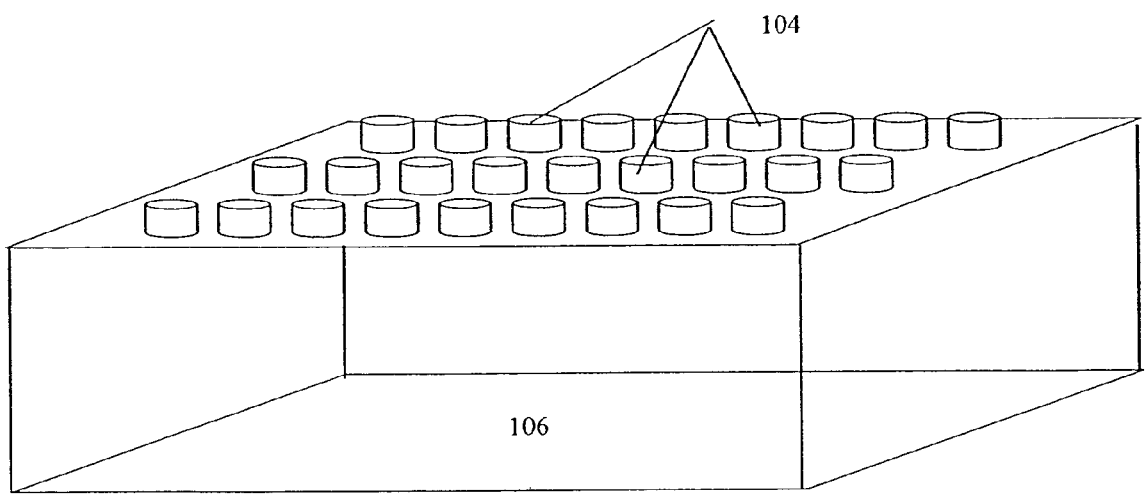

FIG. 14 illustrates, in perspective view, arrays of miniature refractive elements. FIG. 14A shows an array of lenses 100 formed by stamping on the top surface of a bulk infrared element 102. FIG. 14B shows an array of cylinders 104 formed by stamping on the top surface of a bulk infrared element 106.

Figure 15A:
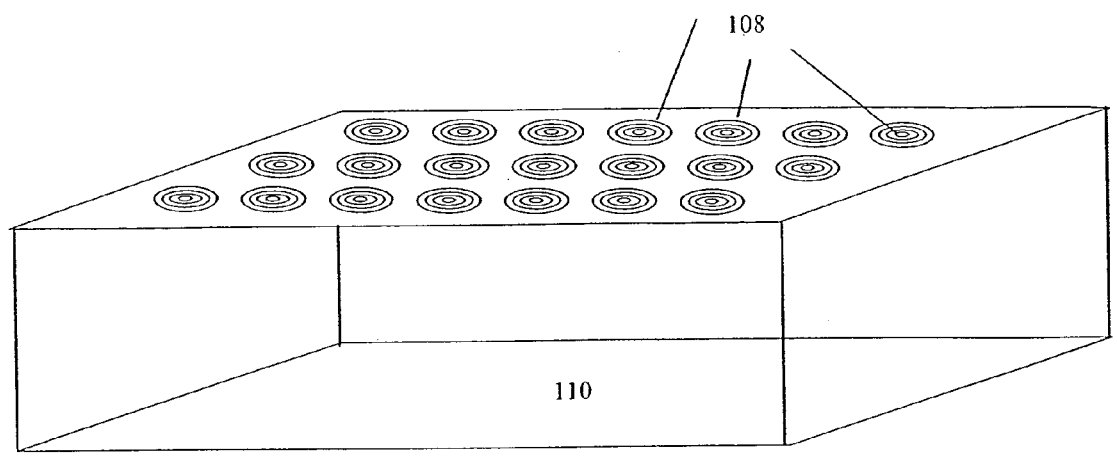
FIG. 15 illustrates arrays of diffractive or binary optical elements, on the surface of an infrared element, made by the forging system of the present invention.
Figure 15B:
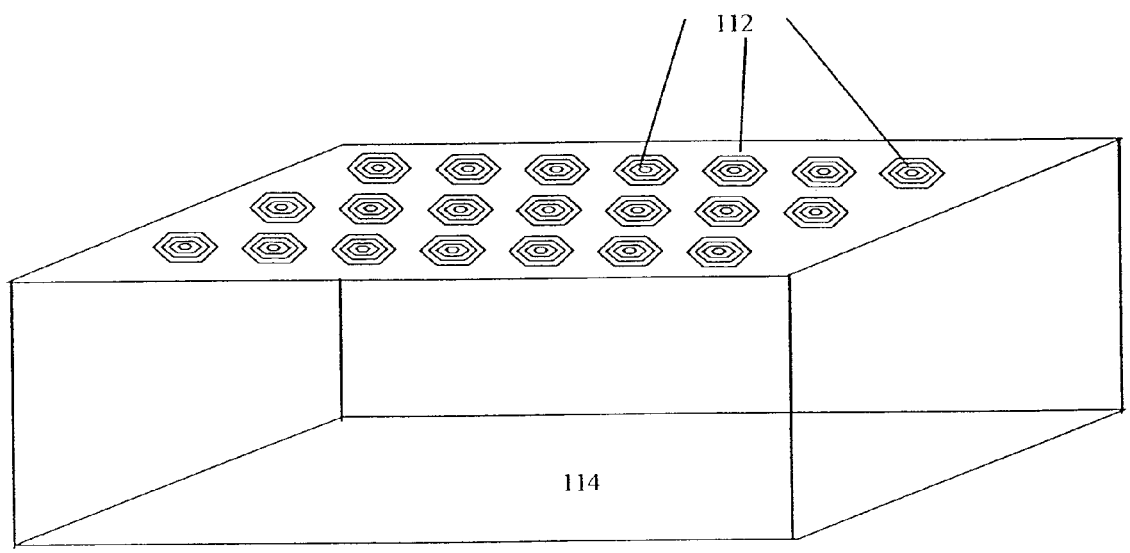
Figure 16A:
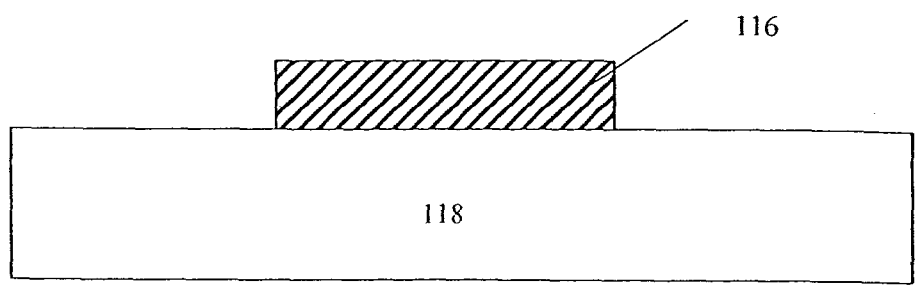
FIG. 16 illustrates cold worked integrated optical elements, made by the system of the present invention.
Figure 16B:
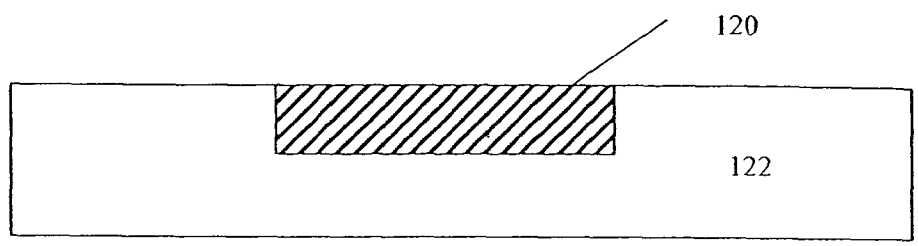
Figure 16C:
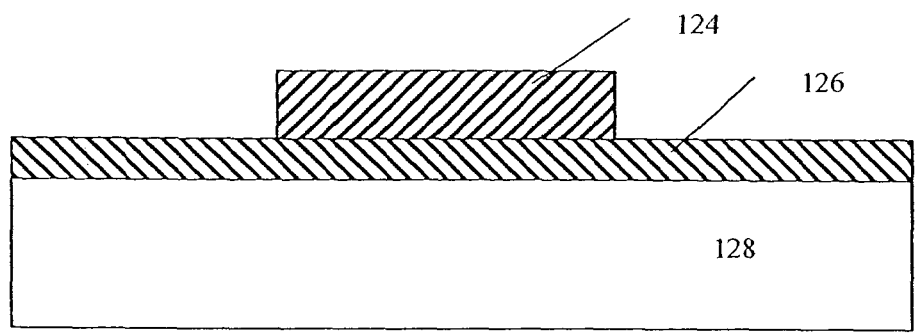
Figure 16D:
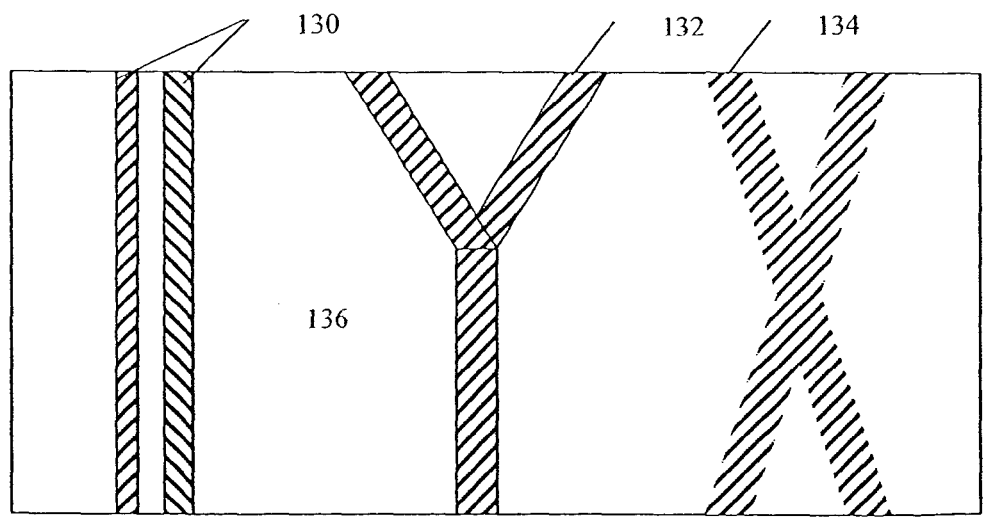

FIG. 15 illustrates, in perspective view, arrays of diffractive or binary optical elements. FIG. 15A shows an array of circular elements 108 formed by press forging on the top surface of a bulk infrared element 110. FIG. 15B shows an array of hexagonal elements 112 formed by press forging on the top surface of a bulk infrared element 114.

FIG. 16 illustrates the geometries of infrared wave guiding elements that are similar to the ones used in Integrated Optics in the visible range and that can be fabricated by the methods of the present invention. All of the elements illustrated in FIG. 16 consist of thin optical waveguides that are placed on a relatively thick substrate that could be a single crystal or a cold pressed sample. FIG. 16A illustrates, in cross section, a thin waveguide 116 on a substrate 118. Waveguide 116 is formed by pressing (e.g. as shown in FIG. 7 or FIG. 9) and is then attached (e.g. by applying light pressure) on substrate 118. FIG. 16B illustrates, in cross section, a waveguide 120 embedded in a substrate 122. A groove is formed on the top of substrate 122, using cold working. Waveguide 120 is formed by pressing (again as shown in FIG. 7 or FIG. 9) and is pressed into the groove. FIG. 16C illustrates, in cross section, a structure of two layers 124 and 126 on a substrate 128. The method of fabrication of the structure of FIG. 16C is similar to the one used to fabricate the structure of FIG. 16A, but in this case two thin layers 124 and 126, of different compositions (and different indices of refraction) are pressed on substrate 128. FIG. 16D illustrates, in plan view, parallel waveguides 130 and couplers 132, 134 inside a substrate 136. The fabrication of the structure of FIG. 16D is similar to the fabrication of the structure of FIG. 16B, but the grooves pressed on the top of substrate 136 are more complex (and so are thin waveguides 130, 132, 134 that are pressed into the grooves). Several steps of cold working are needed to fabricate all these elements.

FIG. 17 illustrates the fabrication of a hybrid optical element that may include the fabrication of a "surface" element on one of the faces of a "bulk" element. FIG. 17 illustrates the fabrication, by press forging between two dies 76 & 66, as in FIG. 11A, of a diffractive element 142 on the flat surface of a piano-concave lens 144.

Figure 11A:
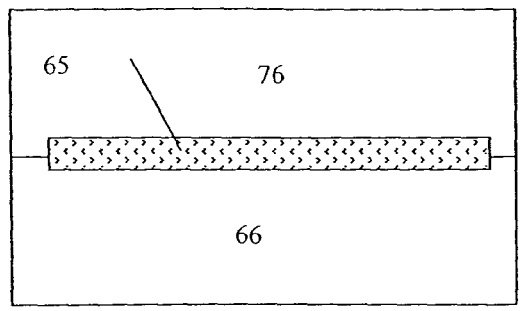
FIG. 11 illustrates the forge pressing of various "bulk" elements (a sacrificial split ring is used in each case but is omitted from the drawing for clarity)
Figure 11B:
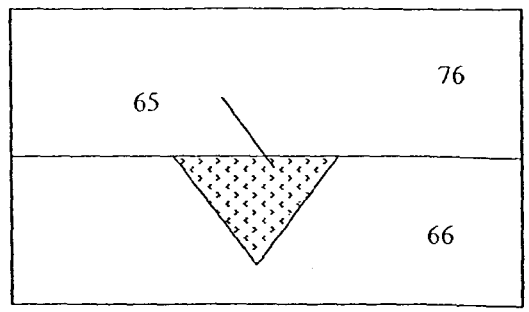
Figure 11C:
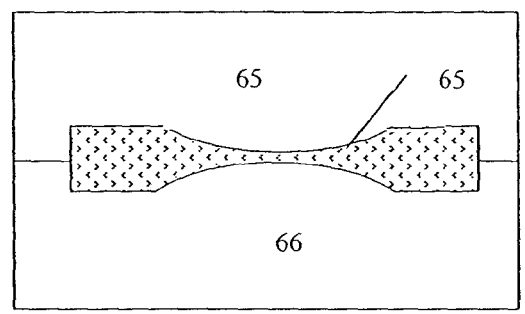
Figure 11D:
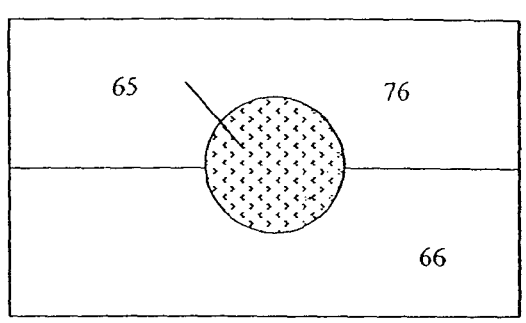
Figure 11E:
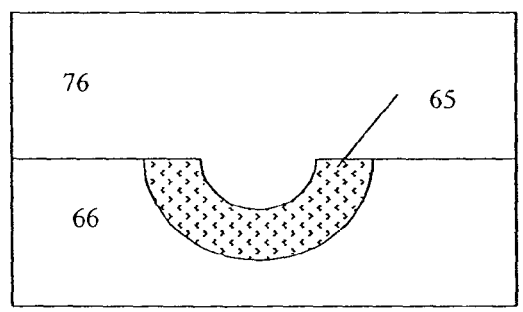
Figure 11F:
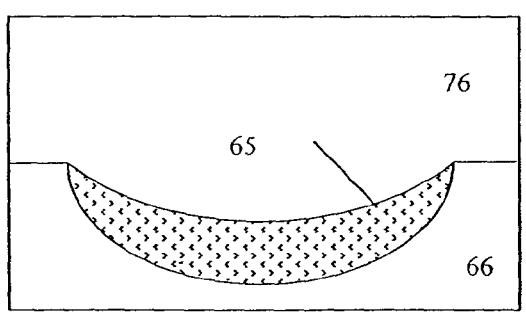
Figure 11G:
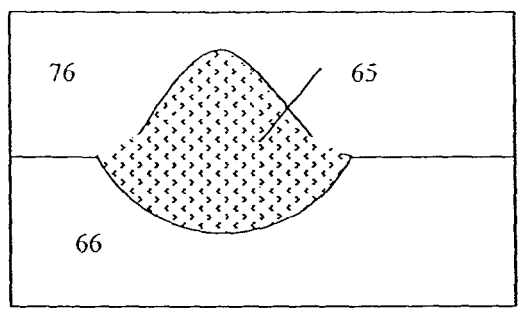
Figure 11H:
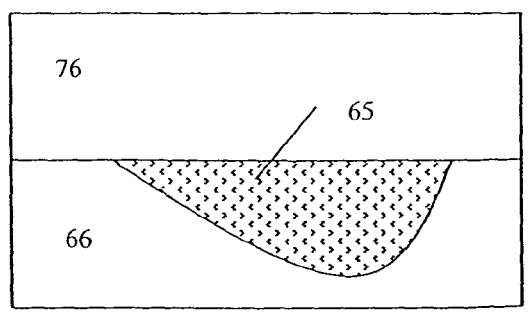
Figure 18A:
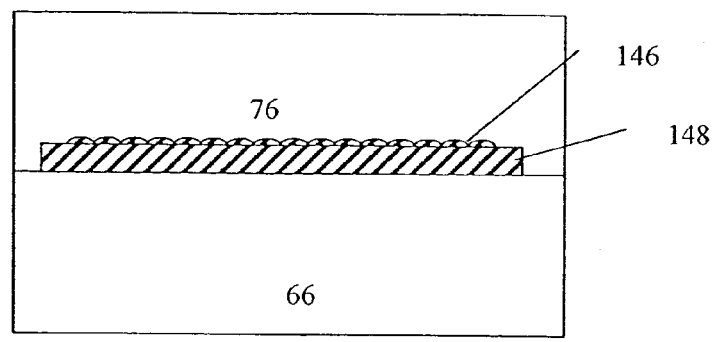
FIG. 18A illustrates forge pressing of refractive or diffractive optical elements on the surface of a waveguide.
Figure 18B:
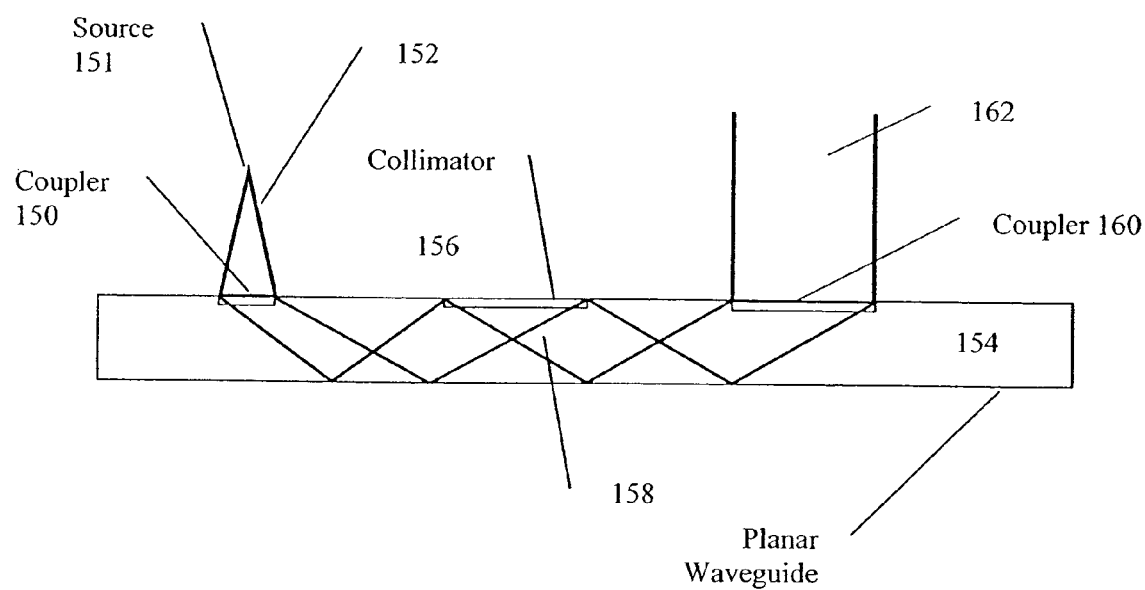
FIG. 18B shows a planar optical element with two coupling elements and a collimating element based on surface optical elements.

FIG. 18A illustrates the fabrication of a set of micro-optical elements 146 (refractive or diffractive) on a substrate 148 by press forging or embossing between two dies 76 & 66, as in FIG. 11A. FIG. 18B shows the use of the elements as couplers or as collimating elements on a planar waveguide, thus forming a planar optical element. In this case one element 150 couples a diverging beam 152 emitted from a small source 151 into a thick waveguide 154. Another element 156 collimates a beam 158 that is traveling inside waveguide 154. A third element 160 couples collimated beam 162 outside waveguide 154.

Both the "bulk" and the "surface" elements may be made by mechanically deforming crystals that are highly transparent in the infrared. There are several halides that are useful for this purpose. Some of these are toxic and others are watersoluble. We have found that mixed silver halides of the formula $AgCl_xBr_yI_{1-x-y}$ where $0<x+y<1$ are most suitable because they are malleable, highly transparent in the whole IR range, bio-compatible and insoluble in water. Crystals of different compositions (x, y) have different hardness. For some applications a "harder" compound (e.g. x=0.3-0.7) is selected, and for others—"softer" compound (e.g. x=0.1-0.2). Pure AgCl and AgBr are ductile at room temperature and their elongation ratio is larger than 10%. They can be easily cold worked to form various shapes. The "harder" compounds mentioned above have lower ductility at room temperature, and they often crack when excessive stress is applied. The ductility of these compounds increases when the temperature is raised to 50-200° C., and in particular when the temperature is raised to the 120° C. to 180° C. range that is optimal for press forging. At such relatively low temperatures the elongation ratio increases above 10% and the crystals can be mechanically deformed without cracking. For some of the "harder" compounds, such as $AgCl_{0.5}Br_{0.5}$, the press forging should be carried out more slowly than for the "softer" compounds (e.g. AgBr). In conclusion, all the crystals are sufficiently ductile, at the 120-180° C. temperature range, so that relatively low pressures (typically 0.1-10 tons/cm$^{-2}$) can deform them, without fracture.

Figure 19A:
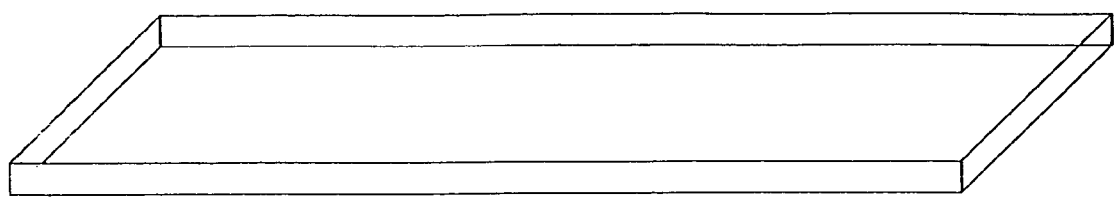
FIG. 19 shows two flat waveguides of the present invention.
Figure 19B:
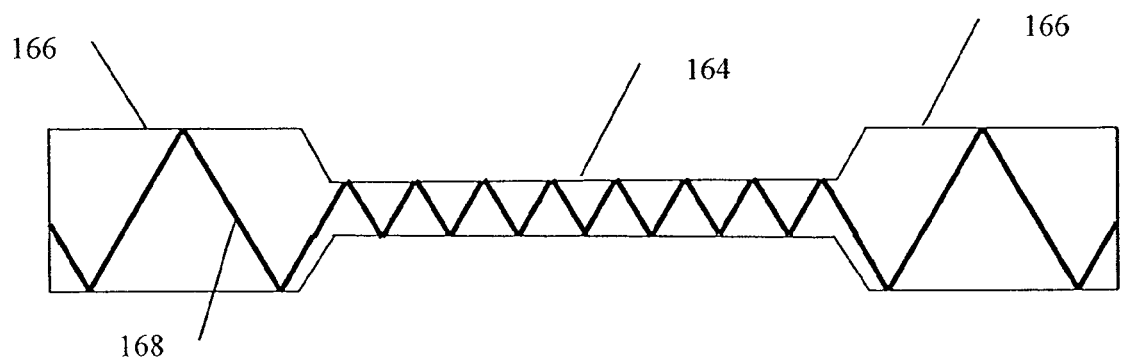

In a series of illustrative experiments we proved the feasibility of deforming single crystals of AgClBr and fabricating "bulk" infrared transmitting elements. We pressed single crystals and polycrystalline samples inside split dies, using top and bottom flat dies that were highly polished. We used metal and non-metal flat dies, and obtained IR transmitting windows of diameters 0.2-7 cm and an excellent optical quality. We formed various convex lenses, of different diameters, ranging between 0.1 cm and 5 cm, by pressing them between highly polished curved top and bottom metal dies inside split dies. The surface quality of the lenses was excellent. These lenses were tested optically in the infrared and exhibited good focusing ability. Much smaller and much larger lenses were easily formed in the same way. By applying pressure we also formed prisms and pyramids. We pressed single crystals and polycrystalline samples (or fibers) between two highly polished parallel plates and formed waveguides of thickness less than 50 μm, as shown in FIG. 19A. We also flattened the central part of a cylindrical fiber to form a tapered waveguide with flattened central segment—as shown in FIG. 19B. All the waveguides had very good transmission in the infrared. In exactly the same manner any infrared element, such as the ones shown in FIGS. 11-13, can be made.

In another series of experiments we used as a stamp a hard metal block that had a set of gratings on one of its surfaces. When this surface was pressed against a crystal of AgClBr, the set of gratings was transferred to the crystal surface. Using exactly the same method, diffractive optics, binary optics and integrated optics elements, such as the ones shown in FIGS. 13-18, can be prepared.

Silver halides are photosensitive, which is why they are used as the photographers' salts in the photographic process. Single crystals of silver halides can be obtained commercially from Crystran in Dorset, UK, or from Janos, Townshend, Vt. Commercial crystals of silver halides darken upon exposure to strong blue or UV light. This darkening reduces the infrared transmission of optical elements prepared from these elements, and renders these elements useless. Monocrystalline silver halides usually are produced by mixing silver nitrate with the appropriate acid (hydrochloric, hydrobromic or hydroiodic). The resulting precipitates are washed, dried, melted, and the single crystals of pure AgCl, AgBr or AgI are grown from the melt. Alternatively, a mixture of x part AgCl, and/or y parts AgBr, and/or z parts AgI is used in the same manner to grow a single crystal of mixed halide such as AgClBr. We have found that it is important to use starting materials of exceptionally high purity. For example, batches of $AgNO_3$ purchased from Eastman Kodak Co. of Rochester N.Y. contain metallic impurities such as Fe, Cu, Ni, Pb, Se, Hg, Cr, Zn, in total concentration less than 1 ppm and $SO_4$ in concentration lower than 5 ppm. $AgNO_3$ of similar purity can also be purchased from Merck KGaA of Darmstadt, Germany and from vendors in the US who distribute chemicals obtained from Eastman Kodak Co. under their own name. For the preparation of AgCl, for example, Suprapur HCl obtained from Merck was used. This HCl contains 50 ppm Br (which does not affect the optical transmission of silver halides, and so is not considered an "impurity" as defined herein), less than 5 ppm sulfate (and few other inorganic impurities) and less than 1 ppm metallic impurities. Acids of similar purity may be obtained from other vendors. By careful preparations and by repeated washing in double distilled water of high purity, one may keep the same level of purity in the silver halide powders and in the crystals grown from these powders. It was found that when the total concentration of impurities in the crystals is lower than 10 ppm, then the crystals are almost insensitive to light. The same holds for the polycrystalline elements made by mechanical deformation. Also, the very low concentration of impurities guarantees that the infrared transmission of the elements is extremely high. On the other hand, crystals prepared from $AgNO_3$, which is not so pure, will be somewhat sensitive to light.

The present invention also relates to bulk ATR elements and thin flat waveguides for use in evanescent wave spectroscopy.

FIG. 19A is a schematic illustration of a flat waveguide constructed and operative in accordance with one embodiment of the present invention. The waveguide is a thin plate formed of any IR transmitting material. Preferably, the waveguide is formed of a flexible IR transmitting material, such as a mixed silver halide of the formula $AgCl_xBr_yI_{1-x-y}$, where $0<x+y<1$. One example of a suitable mixed silver halide is $AgCl_{0.3}Br_{0.7}$. The addition of about 1-3% of iodine is believed to improve the transmissivity and the mechanical properties of this mixed halide. Alternatively, IR transmitting glass or other IR transmitting materials, such as crystalline KRS5, as manufactured by Janos Technology Inc., Townshend, Vt., may be used. However, this latter material is less desirable due to problems of toxicity and aging.

It is a particular feature of the present invention that the waveguide has a substantially planar surface. This provides a better sampling area and increases the sensitivity of the waveguide by almost a factor of 10, as compared with that of a substantially cylindrical fiber. According to one embodiment of the present invention, the cross-section of the waveguide is substantially rectangular.

Preferably, the waveguide is between about 20 microns and about 1 mm thick. Most preferably, the waveguide is between about 100 and 500 microns thick.

FIG. 19B shows schematically, in cross section, a waveguide 164 constructed and operative in accordance with an alternative embodiment of the present invention. Waveguide 164 is a flexible, thin plate, which merges into ends 166 of greater thickness for easier coupling of light 168 during use. This flat waveguide could be constructed by pressing the central part of an optical fiber, inside a sacrificial split ring, and in this case the two ends are cylindrical in shape.

Figure 20:
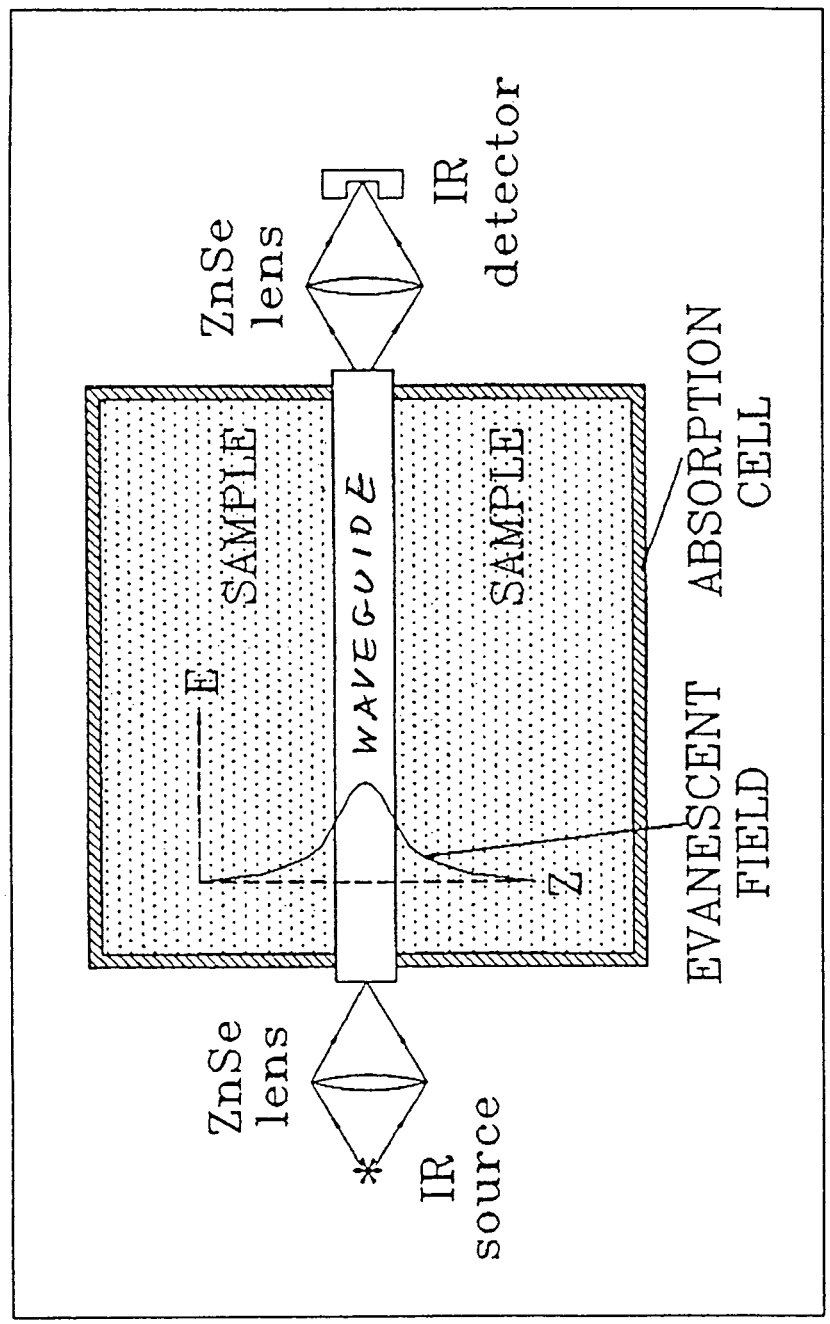
FIG. 20 is an illustration of a cell that is used for ATR measurements: the sensing element was formed by forging inside a sacrificial split die.

FIG. 20 shows a cell that can be used for ATR measurements. The cell incorporates a thin waveguide, such as the one shown in FIG. 19B, that serves as a sensor element. A sample (e.g. fluid) is introduced into the cell, so that it covers the sensing element. The cell is inserted into an FTIR spectrometer for IR absorption measurements.

Figure 3:
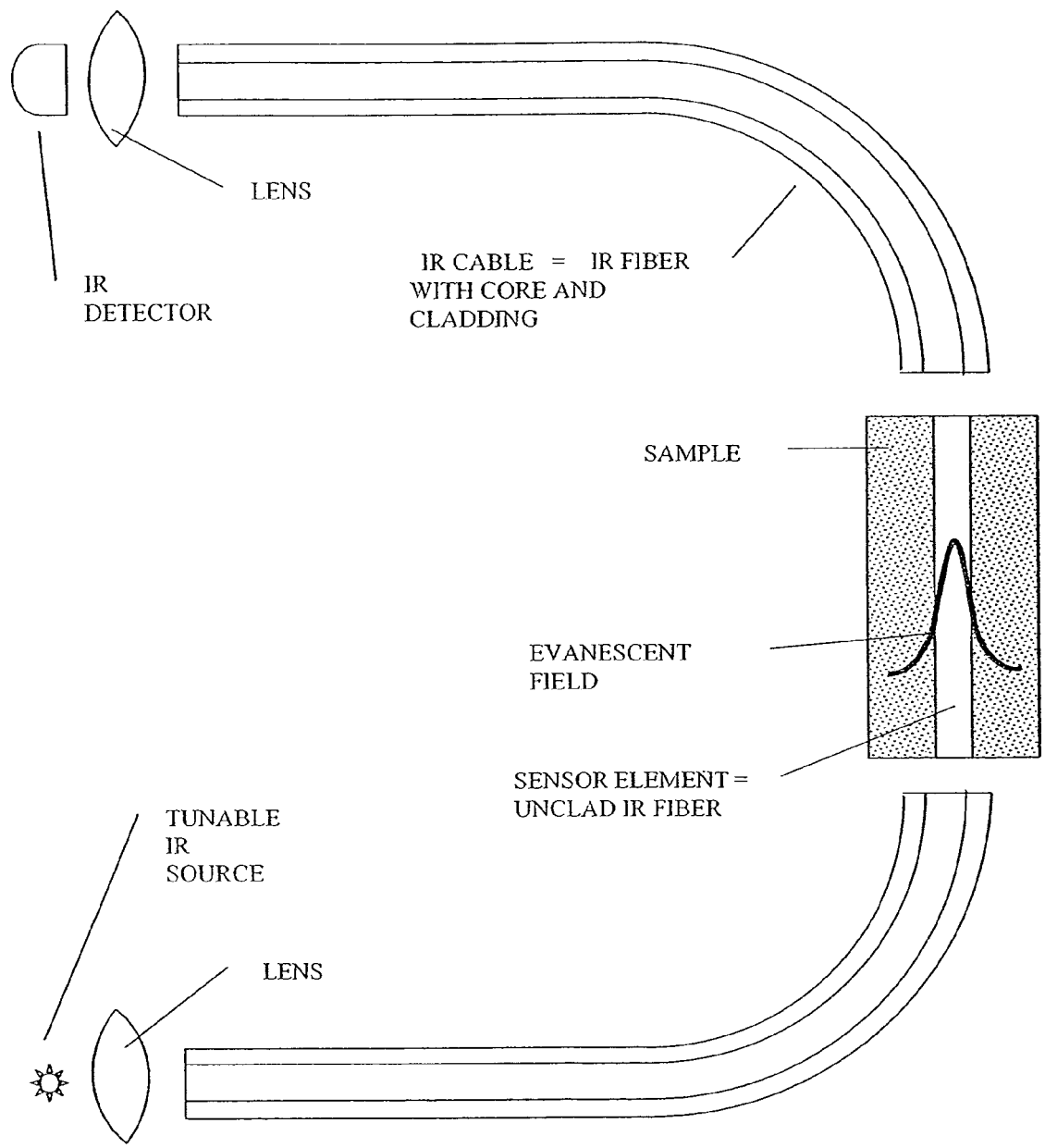
FIG. 3 is a schematic diagram of a prior art FEWS system.
Figure 4A:
FIG. 4 shows six different prior art fiber optic sensor elements.
Figure 4B:
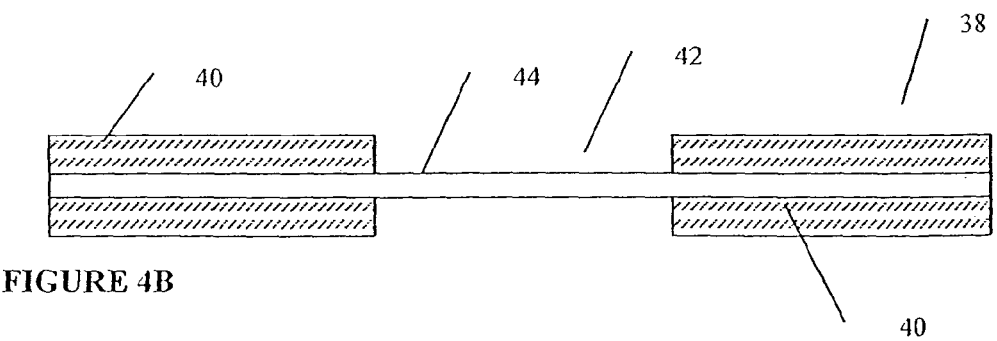
Figure 4C:
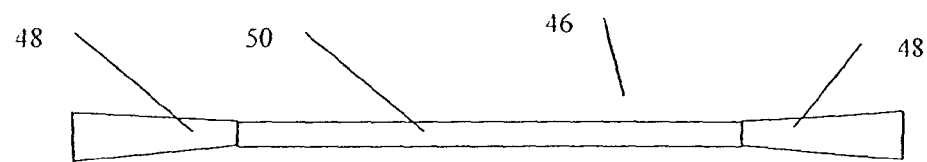
Figure 4D:
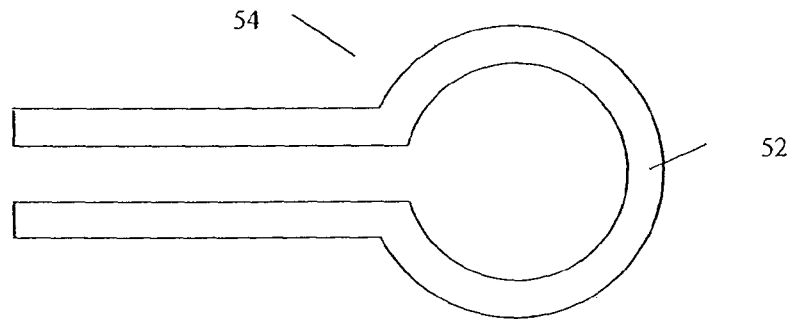
Figure 4E:
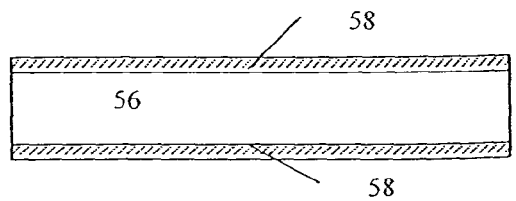
Figure 4F:
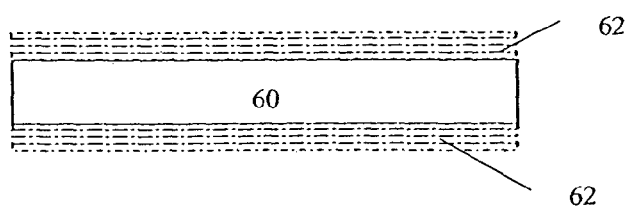

Alternatively, ends 166 of waveguide 164 are coupled optically to the IR source and the IR detector of the FTIR spectrometer using long, flexible optical fibers. This is similar to the setup shown in FIG. 3, but making use of the novel ATR elements that shown schematically in FIG. 19B.

Waveguide 164 is used for spectroscopy of a sample such as a body tissue, remotely from the spectrometer, by placing one of the flat surfaces of waveguide 164 in direct contact with the body tissue.

We have found that the sensitivity of the waveguide depends, in part, on its thickness t. The following experiment was carried out which proved this point. As shown schematically in FIG. 19B, a flat waveguide was formed from an IR transmitting multimode unclad polycrystalline silver halide fiber, made of $AgCl_{0.4}Br_{0.6}$. The original diameter of the fiber was 900 microns. The fiber was cut into five pieces, and the center portion of each was press forged between two flat and polished dies, to 10 form flat waveguides 0.88 mm, 0.70 mm, 0.44 mm and 0.32 mm thick.

Spectra were acquired on a commercial Nicolet model 5PC FTIR spectrometer. The waveguide was inserted into an absorption cell, similar the one shown schematically in FIG. 20. The sensing length of the waveguide was 80 mm. The absorption cell was introduced into the spectrometer and two ZnSe lenses of 25 mm focal length and 25 nm diameter were used. One lens was used to focus the FTIR beam onto the input face of the waveguide, and a second lens, to focus the output beam from the end face of waveguide onto the detector of the FTIR. The spectral resolution of the spectrometer was 4 cm$^{-1}$ and, for each measurement, 60 scans were averaged in order to reduce the noise level.

For each waveguide, the absorbance of ethanol was measured. The waveguide was inserted into the cell and the background spectrum of the dry cell was taken. Ethanol was inserted into the cell and its spectrum taken. The cell was then cleaned with distilled water and dried with high-pressure nitrogen gas.

Figure 21A:
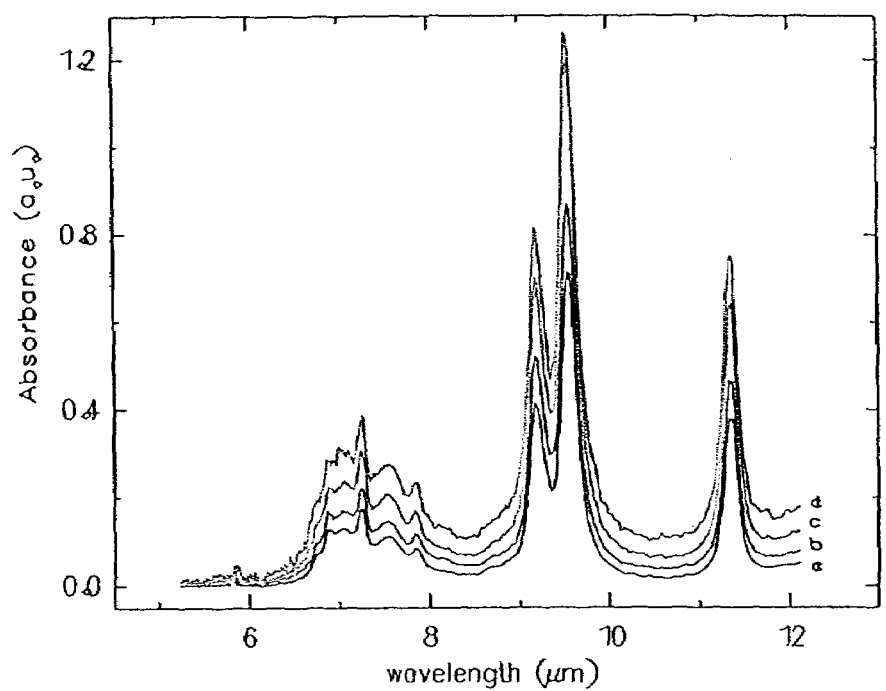
FIG. 21 shows graphic representations of the absorbance of ethanol as a function of waveguide thickness.
Figure 21B:
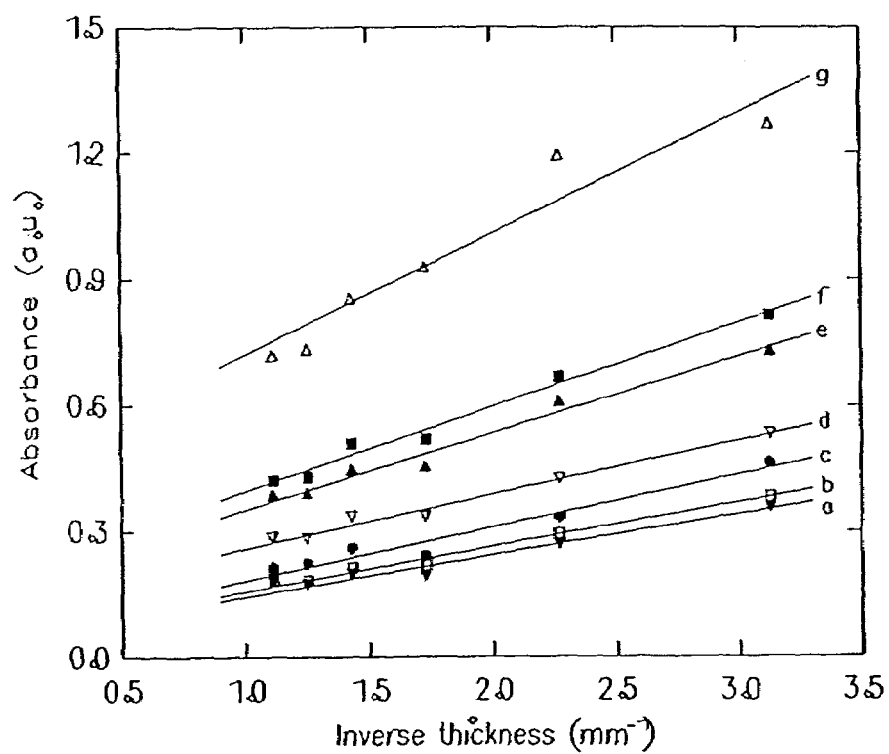

The resultant absorption spectra of ethanol for different waveguide thickness values are shown in FIG. 21A with waveguides of thickness (a) 900 µm, (b) 700 µm, (c) 440 µm, and (d) 320 µm. As can be seen, the ethanol signal is increased upon decreasing the waveguide thickness. In fact, there is a linear relationship between the absorbance at each absorbance peak of ethanol and the inverse of the waveguide thickness, as shown in FIG. 21B. Thus, the absorbance with a 0.32 mm thick waveguide is almost three times the absorbance with a 0.90 mm thick waveguide. In later experiments, thinner waveguides were used. This increased the sensitivity by a factor larger than 10.

According to a preferred embodiment of the present invention, the flat waveguide is sufficiently flexible and easy to handle. The length of the flat waveguide can vary between 1 cm and 50 cm, or more, and is preferably 10 cm long. The flattened fiber that serves as a sensor can be connected to two optical fibers (as shown, schematically, in FIG. 3). Each of these fibers can be tens of meters long, so that the sensing element can be used for measurements in remote locations.

Waveguides according to the present invention can be made by a number of procedures. A disk or fiber of material can be pressed inside a sacrificial split die to flatten it into a waveguide.

Yet another method is to form a very thin waveguide layer of an IR transmitting material on a flat substrate, as illustrated FIG. 22, which shows a bromine rich $AgCl_xBr_{1-x}$ film waveguide 176 on a chlorine rich $AgCl_yBr_{1-y}$ (y>x) substrate 178. Substrate 178 may be flexible or rigid, and may consist of any material having a lower index of refraction than that of the material of waveguide 176. A thin waveguide 176 of about 20 micron thickness can be formed by diffusion or deposition of the IR transmitting material onto the top of substrate 178. Such a waveguide, on a substrate shaped like a microscope slide, is particularly useful for diagnosis or analysis of blood samples, or other organic or biological fluids.

As a non-limiting example, a silver halide, such as bromine-rich $AgCl_yBr_{y-1}$, can be diffused or deposited on a flat substrate of a chlorine-rich $AgCl_xBr_{x-1}$, (x being larger than y), where the substrate has a lower index of refraction. The diffused or deposited layer is suitable as an IR transmitting waveguide according to the present invention.

Figure 22A:
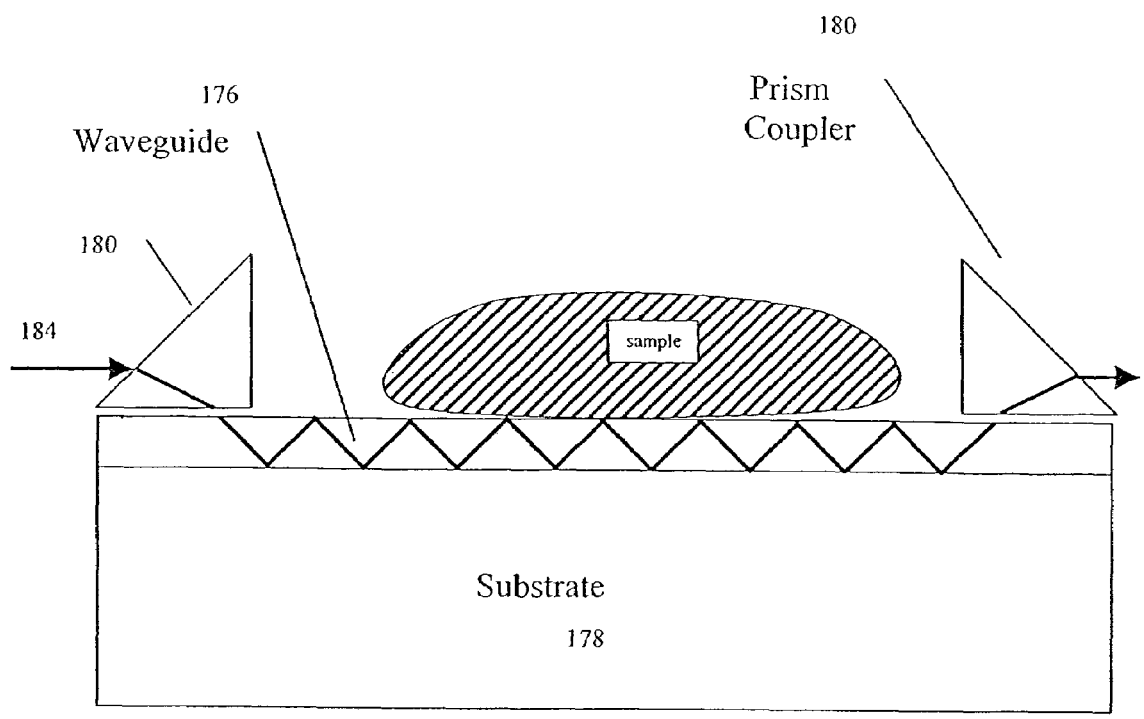
FIG. 22 is a schematic illustration of two embodiments of a thin and flat waveguide formed on a substrate.
Figure 22B:
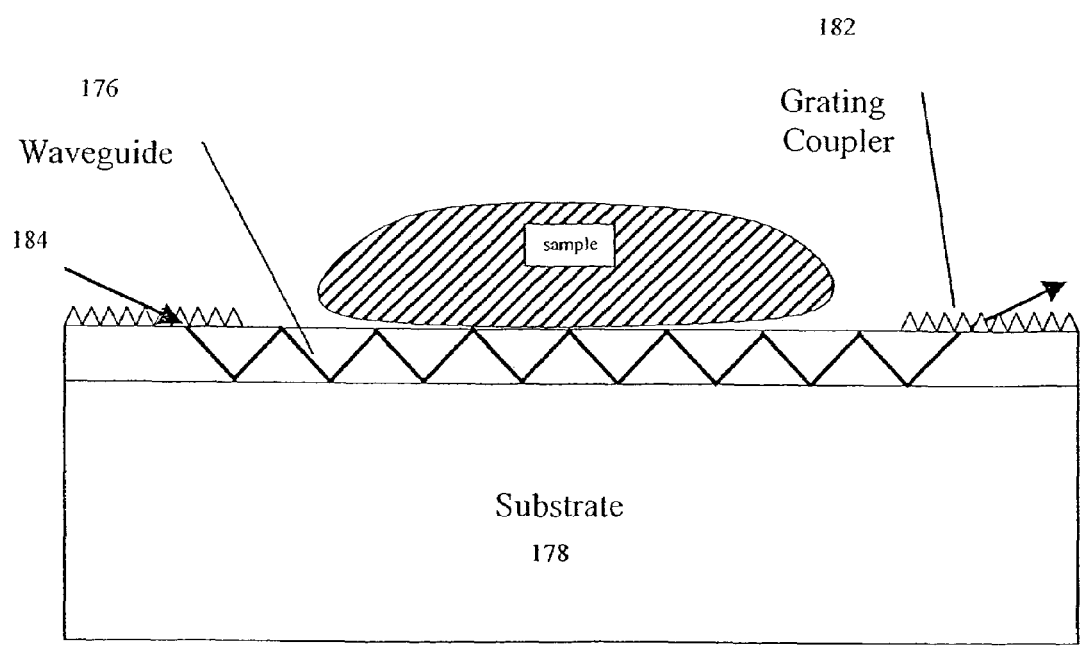

Although it is difficult to couple light in and out of very thin waveguides, it can be done using lenses or other optical elements. Infrared radiation 184 is coupled into and out of film 176 via two prisms 180, as shown in FIG. 22A, or via two sets of gratings 182, as shown in FIG. 22B.

The waveguides of the present invention are particularly useful for monitoring organic pollutants in water and are capable of measuring quantities as low as 10 parts per billion, substantially less than conventional monitoring devices. They are also particularly useful for real time measurements of levels of various chemicals, such as cholesterol, uric acid, proteins, and so on, in the blood, as mentioned below. Furthermore, they are suitable for gas analysis in various samples and for monitoring and controlling chemical reactions, such as polymerization etc. This can be done in real time, at lower cost and with greater ease of operation than conventional ATR and FEWS spectroscopy.

Any source of tunable IR radiation can be used as the light source. Preferably, a tunable laser is used because it provides a narrow beam, which increases the sensitivity of the system. However, a hot source and a set of filters or a continuously variable filter can also be used.

The FEWS system discussed above is easily adopted for other applications. For example the system shown in FIG. 3 can make use of thin waveguide 176 of FIG. 22 as a sensing element. This element, in contact with the human skin, can be used for determining the water content or the fat content or other parameters of the skin. This sensing element can be small and disposable. Such a system that is used for measurements in situ and in real time may be used in dermatology.

Thin waveguides (such as the ones shown in FIG. 19) also may be inserted under the epidermis, using a hypodermic needle. The waveguides may be used for measurements of various components, such as glucose, in the interstitial fluid. The sensor elements (shown, for example, in FIG. 3) may even be left in the body for an extended period of time. Periodically they may be connected to the full FEWS system and measurements may then be carried out.

The same system may be easily adapted for cosmetics, for determining skin type and adapting cosmetics to skin types. Silver halides are non toxic and bio compatible, and they are particularly suitable for such medical and cosmetic applications.

One of the applications of the FEWS system is the determination of the diffusion of chemicals into tissue. This is useful in medicine, for topical applied drugs, or in cosmetics, for the study of the diffusion of cosmetics into the skin.

Figure 23:
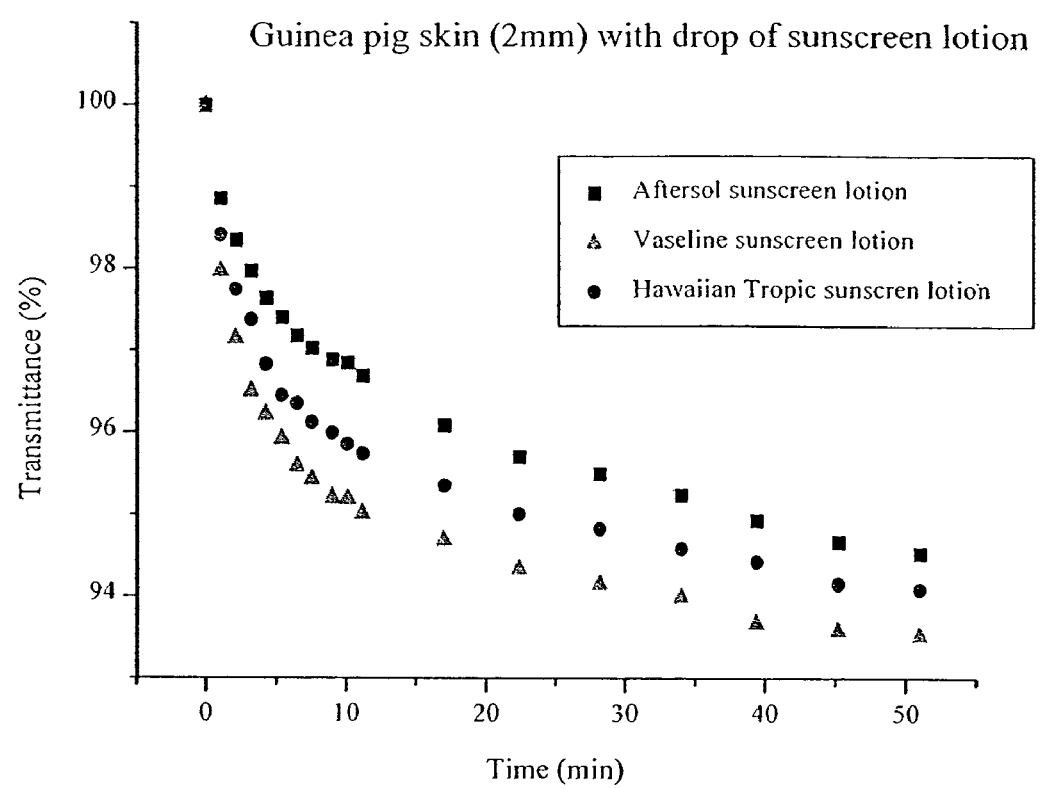
FIG. 23 shows a graphic representation of the penetration of various sunscreen lotions into the skin of a guinea pig, as measured by a FEWS system.

In some illustrative experiments we applied a sunscreen lotion onto the top layer of a 2 mm section of tissue. We attached the sensing element of a FEWS system on the bottom layer of the tissue. With time the sunscreen lotion diffused through the tissue and reached the sensing element. It was easy to follow the diffusion with time. The results of the experiments, using different sunscreen lotions, are shown in FIG. 23. The transmission of the sensor element decreased as the lotion reached its surface.

The same measurements also may be carried out on one side of the tissue. This may be used, for example, for the study of diffusion of various cosmetics into the facial skin.

While the invention has been described with respect to a limited number of embodiments, it will be appreciated that many variations, modifications and other applications of the invention may be made.

What is claimed is:

1. A method of forming an optical element, the method comprising the steps of:
   (a) providing an ingot of at least one silver halide selected from the group consisting of silver chloride, silver bromide, silver iodide, silver chloro-bromide, silver bromo-iodide, silver chloro-iodide, and silver chloro-bromo-iodide and including at most about one part per million of metallic impurities, by steps including:
      (i) mixing silver nitrate with at least one acid selected from the group consisting of hydrochloric acid, hydrobromic acid and hydroiodic acid, to precipitate said at least one silver halide as at least one powder;
      (ii) melting said at least one powder to provide a melt, and
      (iii) cooling said melt to form said ingot; and
   (e) pressing said ingot between an upper die and a lower die while said ingot is confined laterally by a split die.

2. The method of claim 1, wherein said silver nitrate includes at most about one part per million metallic impurities and at most about five parts per million sulfate, and wherein said acid includes at most about one part per million metallic impurities and at most about five parts per million sulfate.

3. A method of forming an optical element, the method comprising the steps of:
   (a) providing an ingot of an ionic crystalline material, and
   (b) pressing said ingot between an upper die and a lower die while said ingot is confined laterally by a split die;
wherein said pressing is effected at a temperature sufficiently high to prevent cracking of said ingot and sufficiently low to prevent darkening of said ingot.

4. A method of forming an optical element, the method comprising the steps of:
   (a) providing an ingot of an ionic crystalline material, and
   (b) pressing said ingot between an upper die and a lower die while said ingot is confined laterally by a split die;
wherein said pressing is effected at a temperature between about 120° C. and about 180° C.

5. A method of forming an optical element, the method comprising the steps of:
   (a) providing an ingot of an ionic crystalline material, and
   (b) pressing said ingot between an upper die and a lower die while said ingot is confined laterally by a split die;

wherein said split die is inert relative to said ingot in a temperature range between about 120° C. and about 180° C., and wherein said pressing is effected at a temperature in said temperature range.

6. A method of forming a plurality of optical elements, comprising the steps of: for each optical element:
  (a) providing a respective ingot of an ionic crystalline material; and
  (b) pressing said respective ingot between an upper die and a lower die while said ingot is confined laterally by a respective split die;
wherein said pressing is effected at a temperature sufficiently high to prevent cracking of said ingots and sufficiently low to prevent darkening of said ingots.

7. A method of forming a plurality of optical elements, comprising the steps of: for each optical element:
  (a) providing a respective ingot of an ionic crystalline material; and
  (b) pressing said respective ingot between an upper die and a lower die while said ingot is confined laterally by a respective split die;
wherein said pressing is effected at a temperature between about 120° C. and about 180° C.

8. A method of forming a plurality of optical elements, comprising the steps of: for each optical element:
  (a) providing a respective ingot of an ionic crystalline material; and
  (b) pressing said respective ingot between an upper die and a lower die while said ingot is confined laterally by a respective split die;
wherein each said split die is inert relative to said respective ingot in a temperature range between about 120° C. and about 180° C., and wherein said pressing is effected at a temperature in said temperature range.

* * * * *